United States Patent
Abdou

(10) Patent No.: US 7,635,366 B2
(45) Date of Patent: Dec. 22, 2009

(54) PLATING SYSTEM FOR BONE FIXATION AND METHOD OF IMPLANTATION

(76) Inventor: M. Samy Abdou, 7790 Doug Hill, San Diego, CA (US) 92127

(*) Notice: Subject to any disclaimer, the term of this patent is extended or adjusted under 35 U.S.C. 154(b) by 226 days.

(21) Appl. No.: 11/025,659

(22) Filed: Dec. 28, 2004

(65) Prior Publication Data

US 2005/0177163 A1 Aug. 11, 2005

Related U.S. Application Data

(60) Provisional application No. 60/533,062, filed on Dec. 29, 2003, provisional application No. 60/551,263, filed on Mar. 8, 2004, provisional application No. 60/603,808, filed on Aug. 23, 2004.

(51) Int. Cl.
*A61B 17/80* (2006.01)
(52) U.S. Cl. .......................................................... 606/71
(58) Field of Classification Search .................. 606/69, 606/70, 71
See application file for complete search history.

(56) References Cited

U.S. PATENT DOCUMENTS

| | | | |
|---|---|---|---|
| 2,248,054 A | 7/1941 | Becker | |
| 3,659,595 A * | 5/1972 | Haboush | 606/71 |
| 4,289,123 A | 9/1981 | Dunn | |
| 5,133,717 A | 7/1992 | Chopin | |
| 5,354,292 A | 10/1994 | Braeuer et al. | |
| 5,364,399 A | 11/1994 | Lowery et al. | |
| 5,545,164 A | 8/1996 | Howland | |
| 5,578,034 A | 11/1996 | Estes | |
| 5,616,142 A | 4/1997 | Yuan et al. | |
| 5,676,666 A | 10/1997 | Oxland et al. | |
| 5,681,311 A | 10/1997 | Foley et al. | |
| 5,681,312 A | 10/1997 | Yuan et al. | |
| 5,713,900 A | 2/1998 | Benzel et al. | |
| 5,735,853 A | 4/1998 | Olerud | |
| 5,928,233 A | 7/1999 | Apfelbaum et al. | |
| 5,954,722 A | 9/1999 | Bono | |
| 5,971,987 A | 10/1999 | Huxel et al. | |
| 5,993,449 A | 11/1999 | Schlapfer et al. | |
| 6,039,740 A | 3/2000 | Olerud | |
| 6,139,549 A | 10/2000 | Keller | |
| 6,152,927 A | 11/2000 | Farris et al. | |
| D440,311 S | 4/2001 | Michelson | |
| 6,224,602 B1 | 5/2001 | Hayes | |
| 6,235,034 B1 | 5/2001 | Bray | |
| D449,692 S | 10/2001 | Michelson | |
| 6,306,136 B1 | 10/2001 | Baccelli | |

(Continued)

FOREIGN PATENT DOCUMENTS

WO 2004/032726 4/2004

(Continued)

*Primary Examiner*—Thomas C Barrett
*Assistant Examiner*—Nicholas Woodall
(74) *Attorney, Agent, or Firm*—Mintz, Levin, Cohn, Ferris, Glovsky and Popeo, P.C.; Fred C. Hernandez

(57) ABSTRACT

A modular bone distraction screw and a plate-based bone fixation device are well adapted for use in the spine. A plate has adjustable length and can accommodate bone settling. The method of use for each device is described and illustrated herein.

27 Claims, 23 Drawing Sheets

U.S. PATENT DOCUMENTS

| | | |
|---|---|---|
| 6,331,179 B1 | 12/2001 | Freid et al. |
| 6,454,769 B2 | 9/2002 | Wagner et al. |
| 6,524,315 B1 | 2/2003 | Selvitelli et al. |
| 6,547,790 B2 | 4/2003 | Harkey, III et al. |
| 6,599,290 B2 | 7/2003 | Bailey et al. |
| 6,602,255 B1 | 8/2003 | Campbell et al. |
| 6,602,256 B1 | 8/2003 | Hayes |
| 6,626,907 B2 | 9/2003 | Campbell et al. |
| 6,652,525 B1 | 11/2003 | Assaker et al. |
| 6,663,632 B1 | 12/2003 | Frigg |
| 6,666,867 B2 * | 12/2003 | Ralph et al. .................. 606/71 |
| 6,695,846 B2 | 2/2004 | Richelsoph et al. |
| 6,855,147 B2 * | 2/2005 | Harrington, Jr. ............. 606/69 |
| 2001/0047172 A1 | 11/2001 | Foley et al. |
| 2002/0055741 A1 | 5/2002 | Schlapfer et al. |
| 2002/0099386 A1 | 7/2002 | Beger et al. |
| 2002/0188296 A1 * | 12/2002 | Michelson ................... 606/71 |
| 2003/0078583 A1 | 4/2003 | Biedermann et al. |
| 2004/0133207 A1 | 7/2004 | Abdou |
| 2004/0204712 A1 * | 10/2004 | Kolb et al. ................... 606/69 |
| 2004/0204713 A1 | 10/2004 | Abdou |
| 2005/0004573 A1 | 1/2005 | Abdou |
| 2005/0010227 A1 * | 1/2005 | Paul ........................... 606/71 |

FOREIGN PATENT DOCUMENTS

| | | |
|---|---|---|
| WO | 2004/062482 | 7/2004 |
| WO | 2004/093702 | 11/2004 |

* cited by examiner

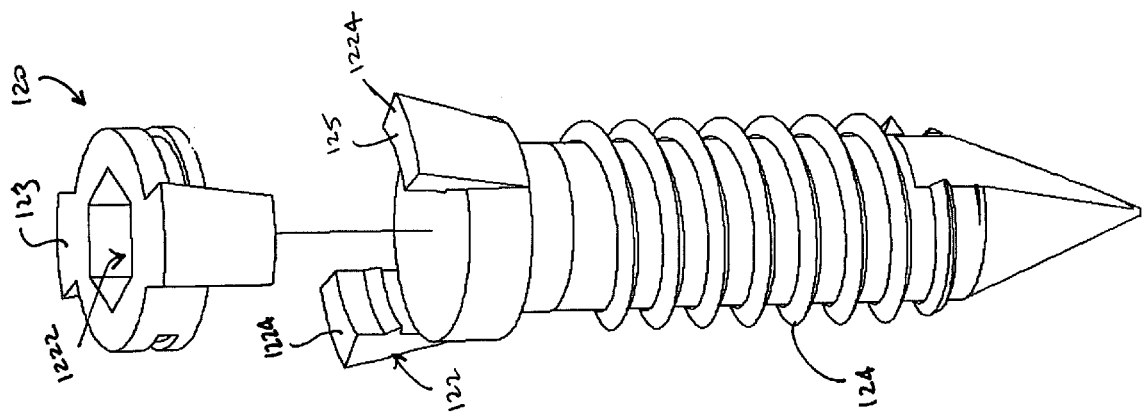
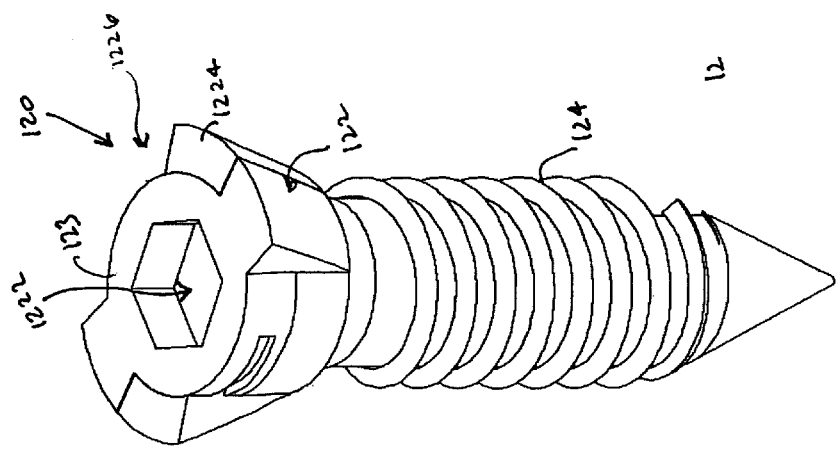
Fig. 3

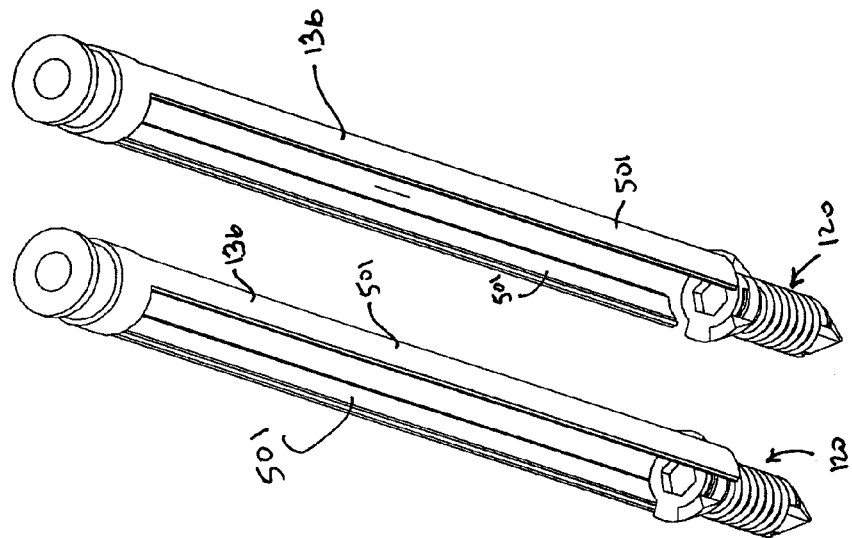
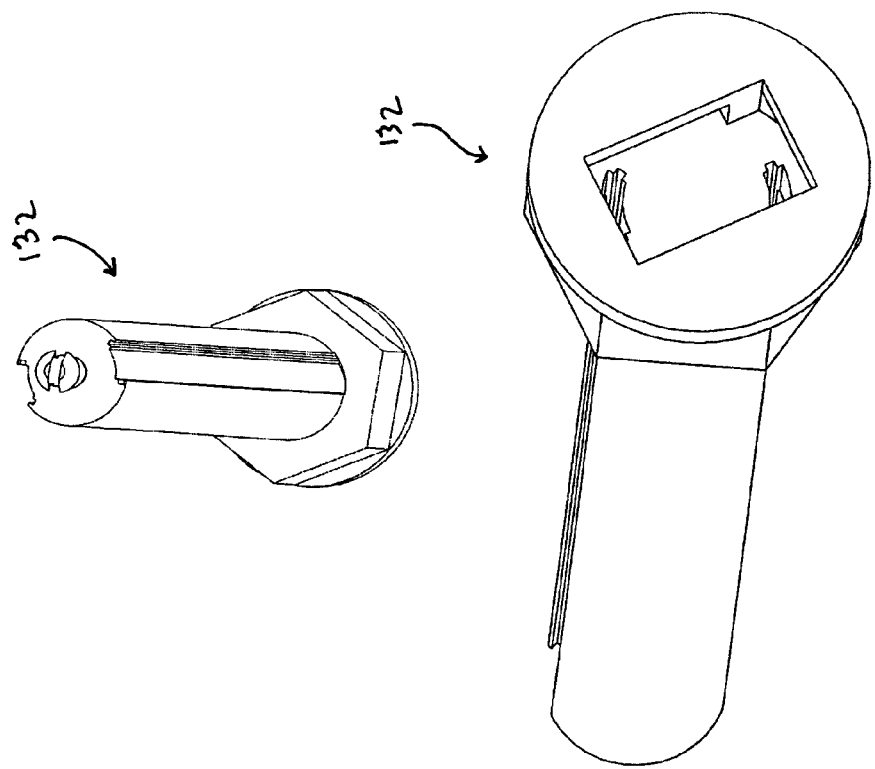
Fig. 4

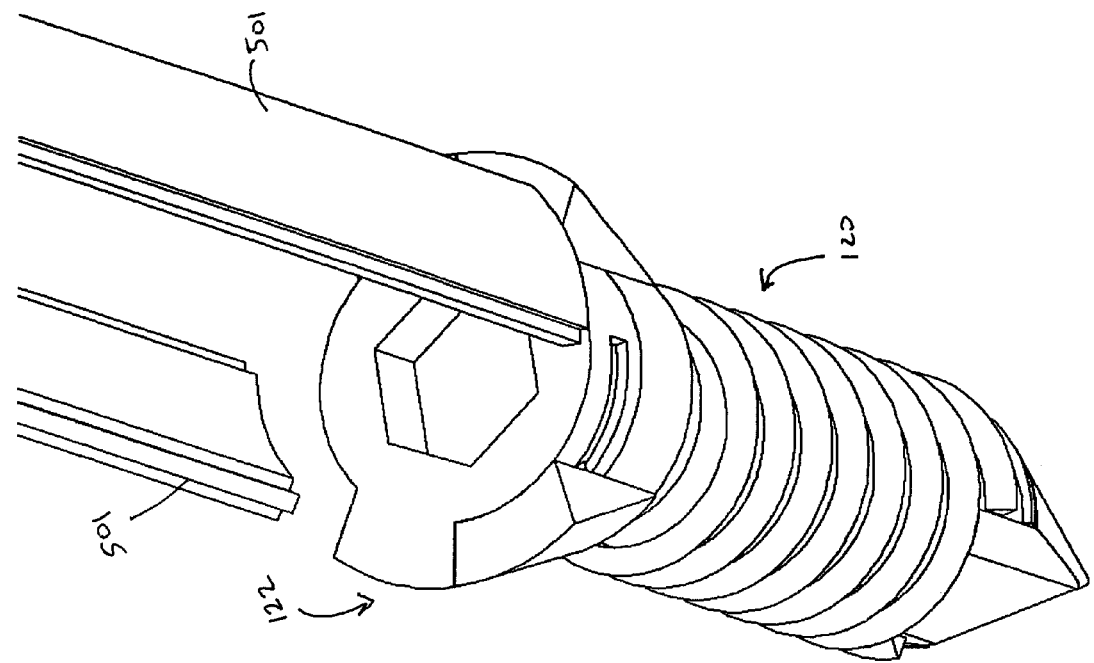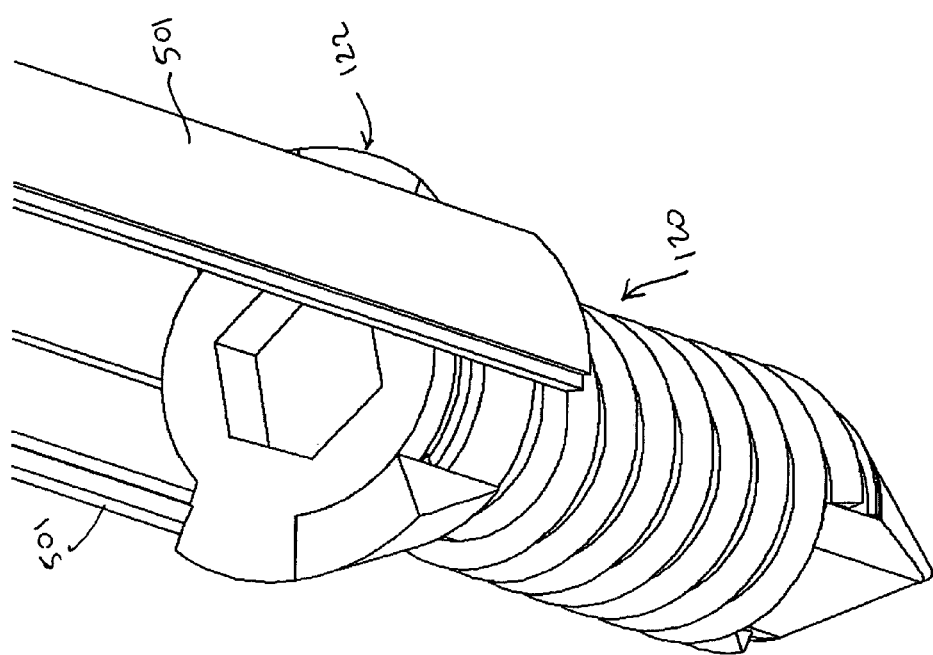
Fig. 5

Fig. 12
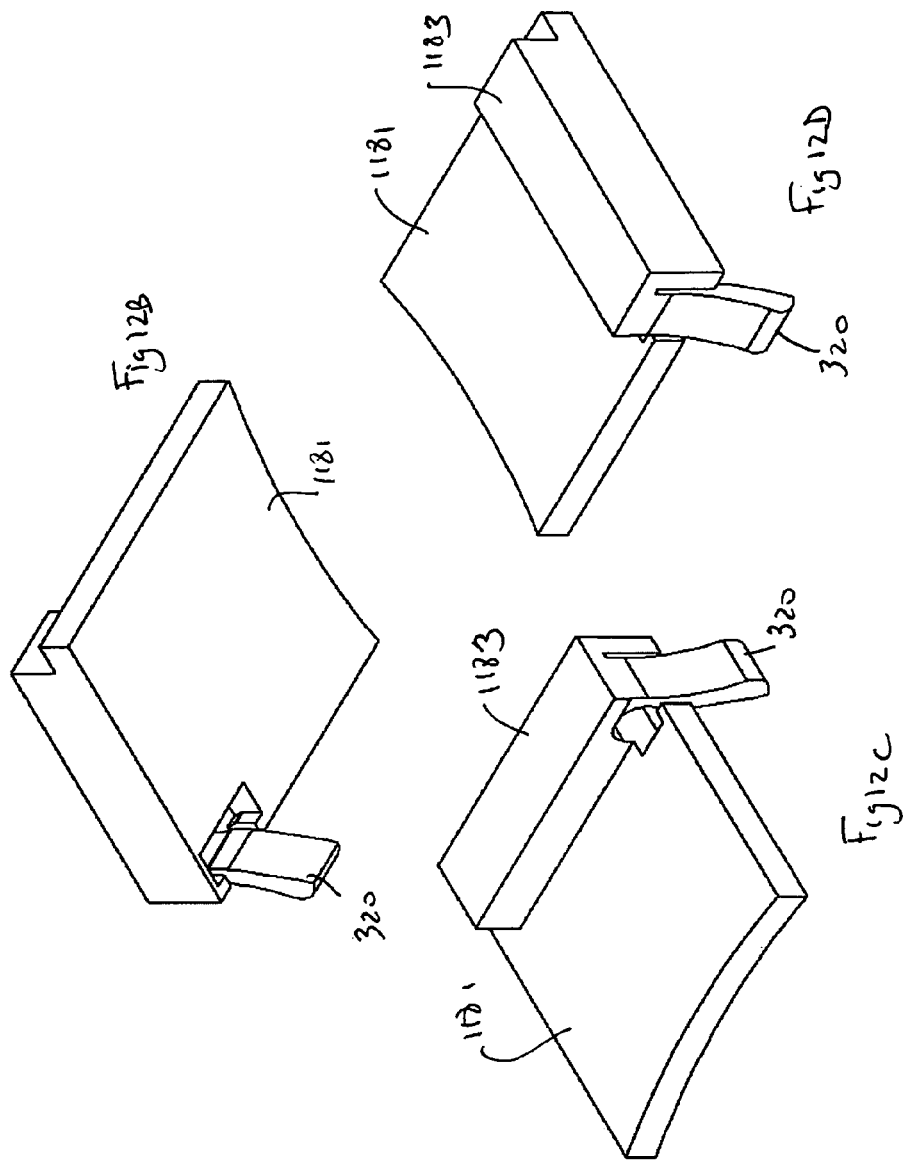
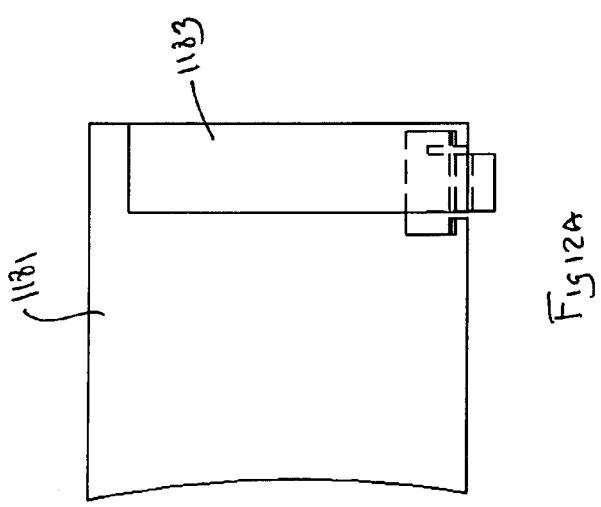

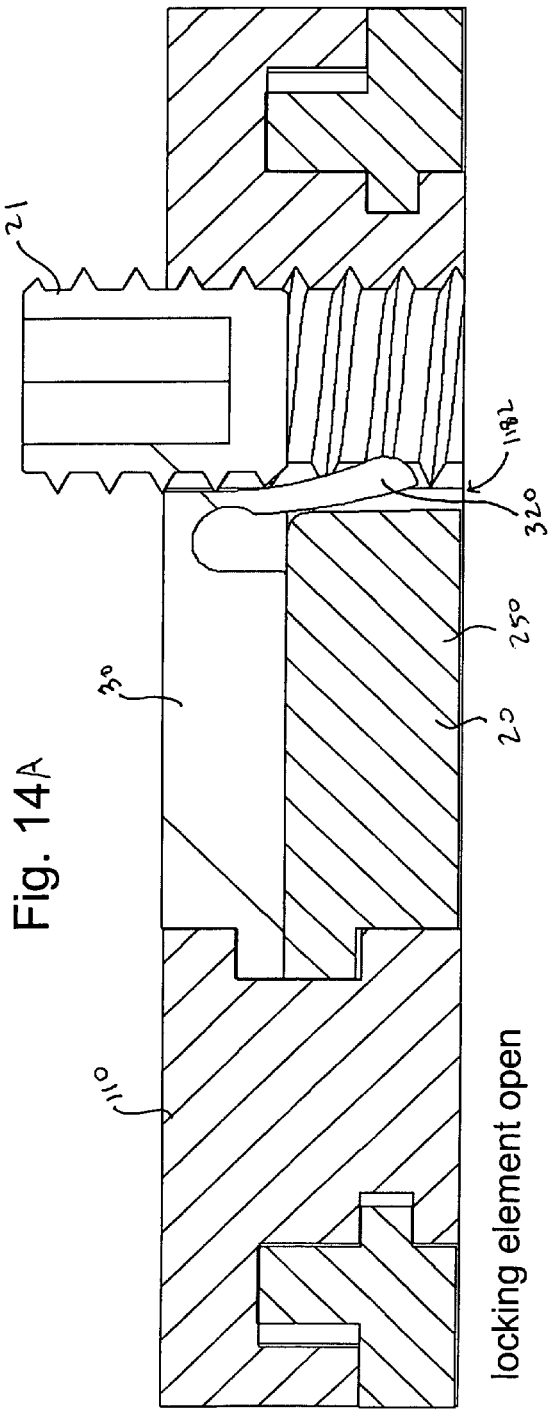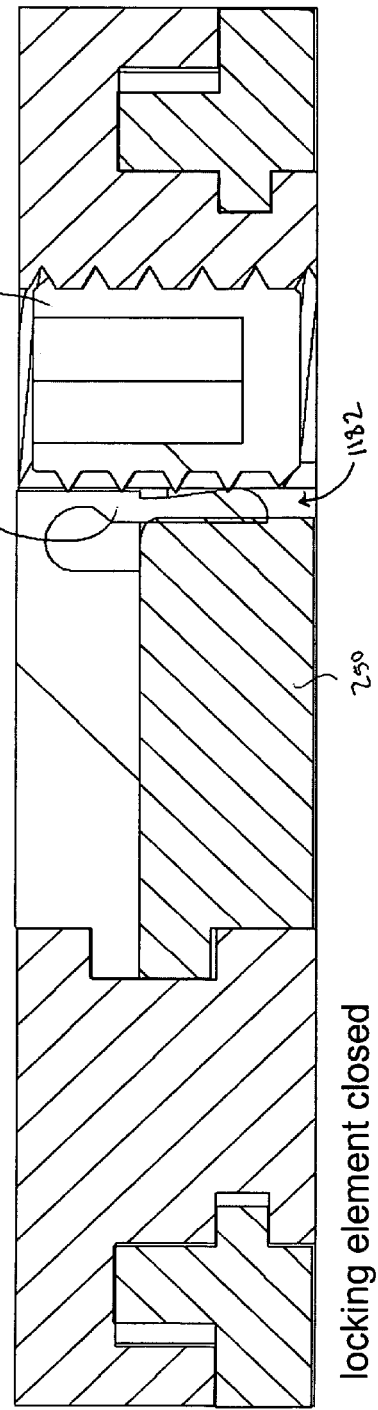
Fig. 14A — locking element open
Fig. 14B — locking element closed

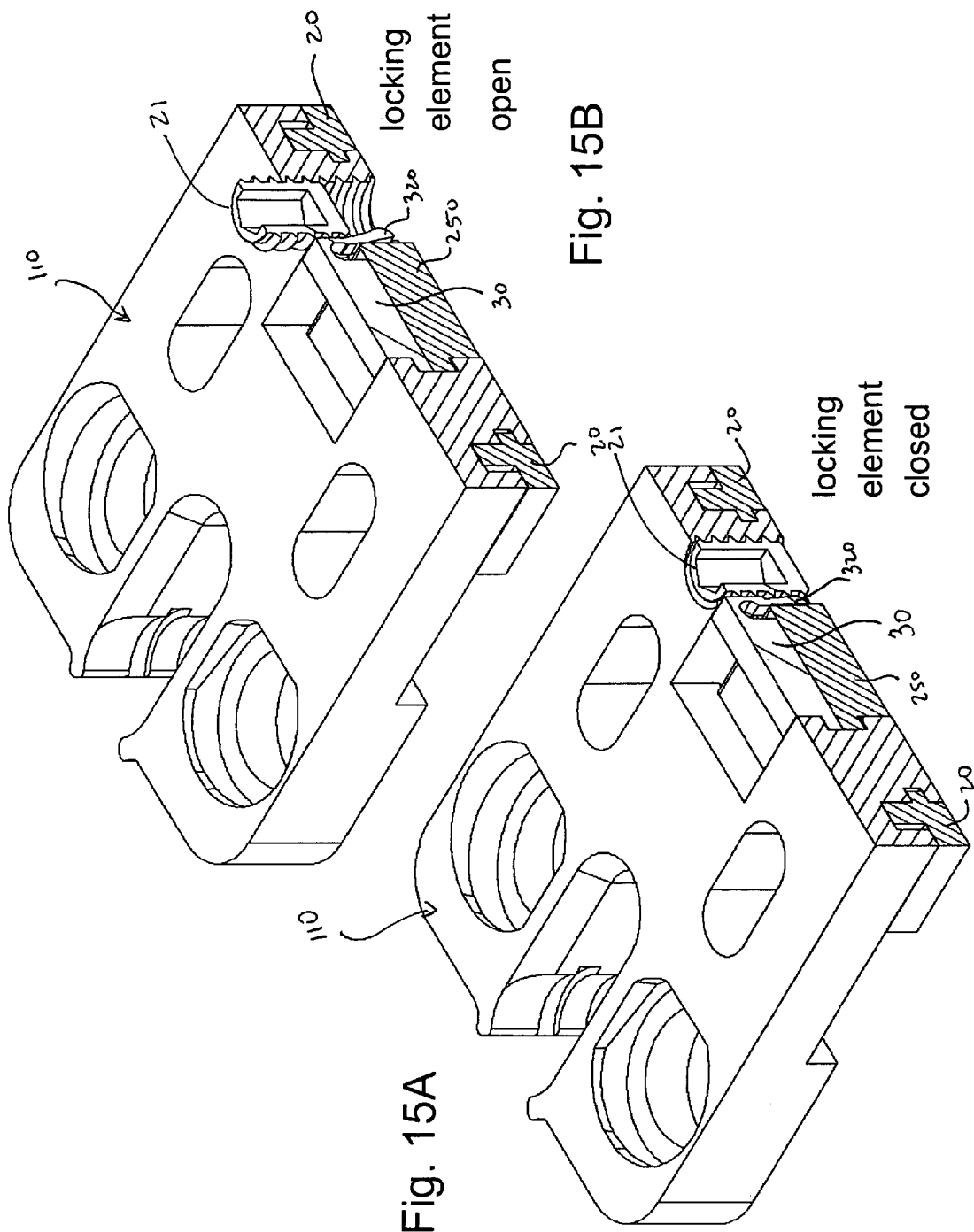

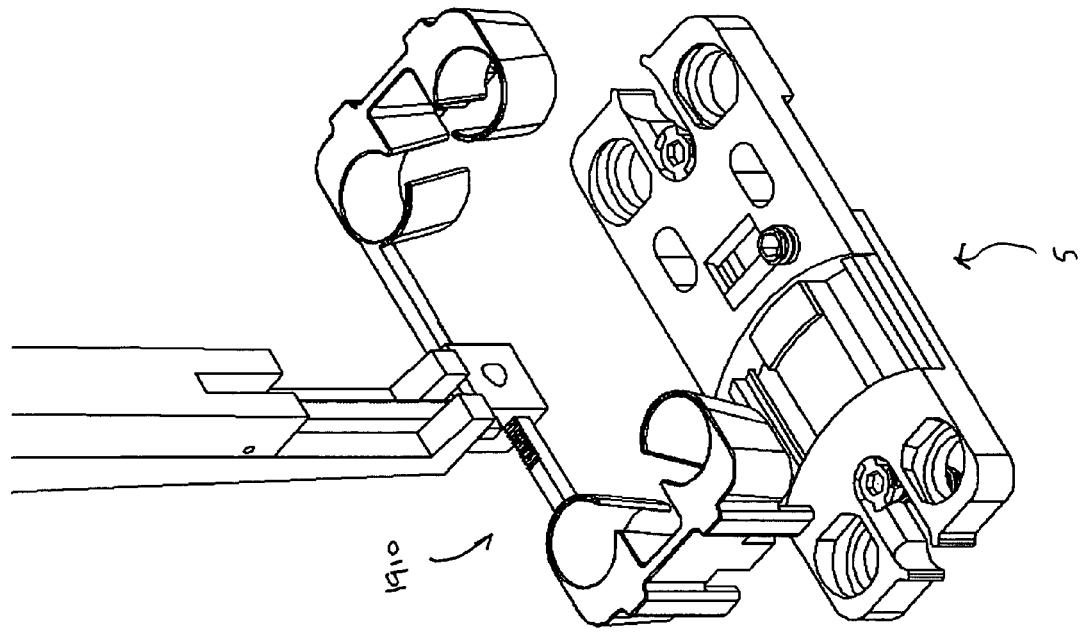
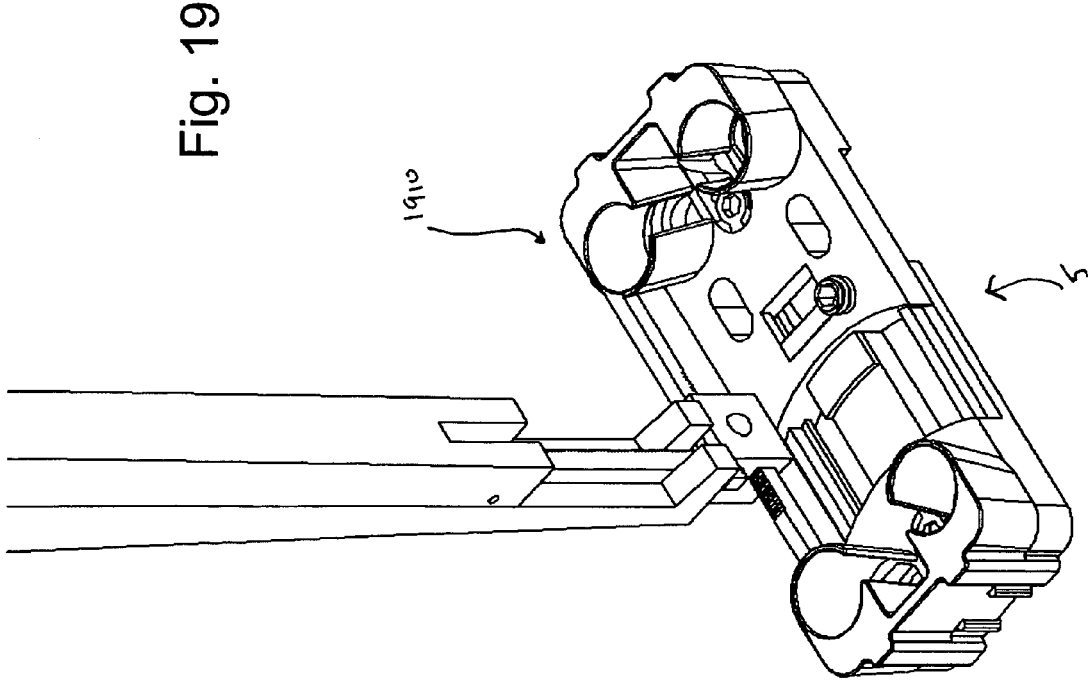
Fig. 19

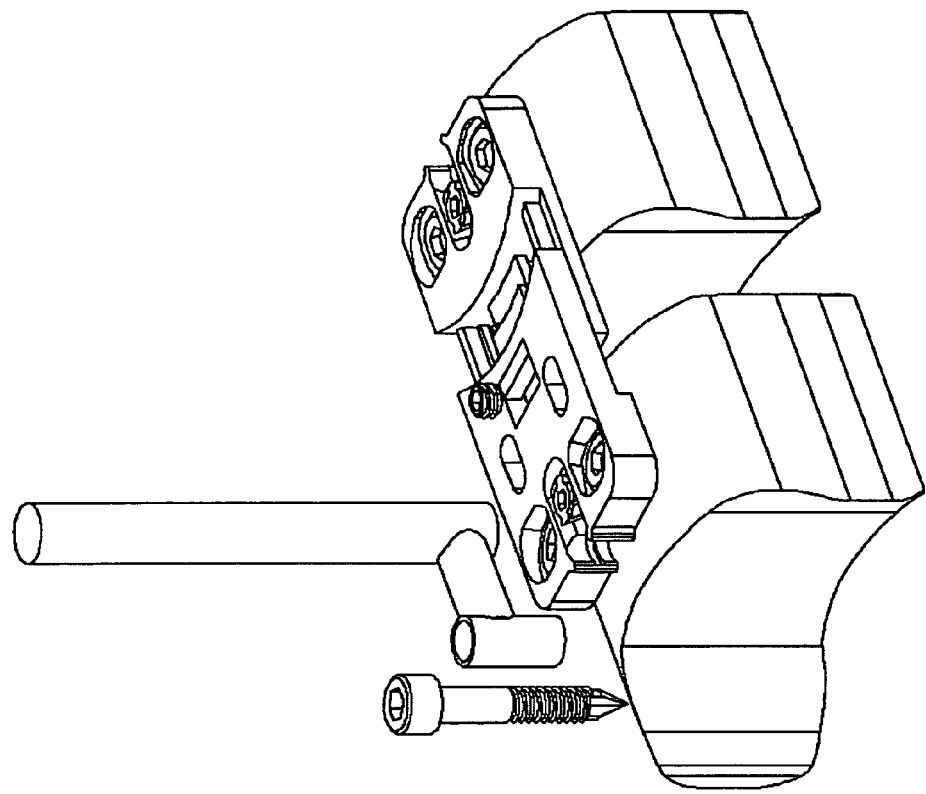
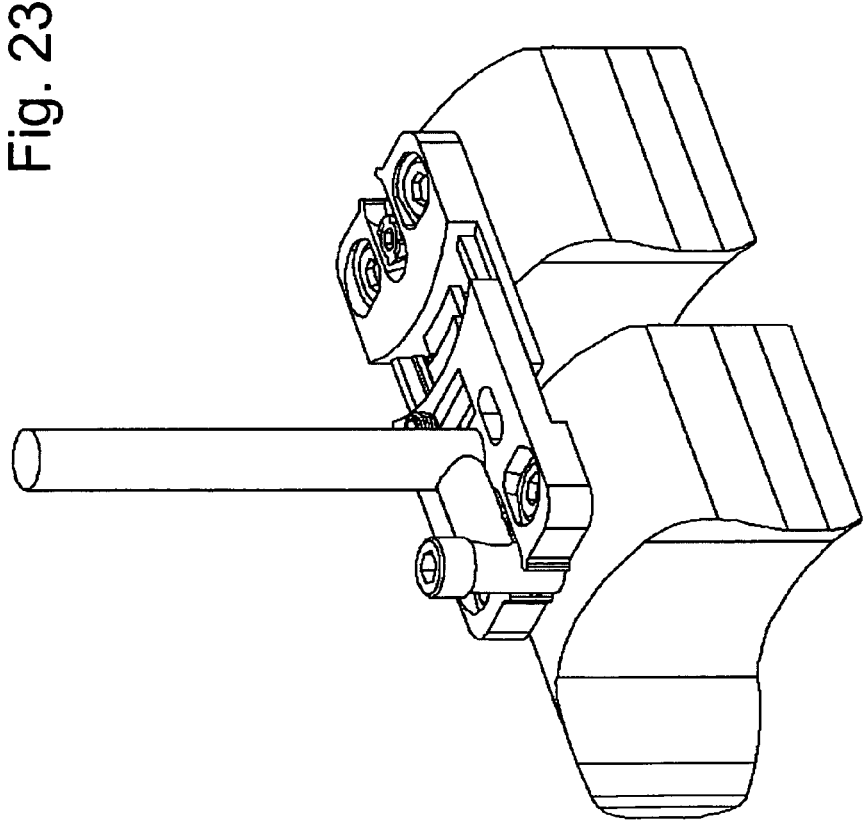
Fig. 23

PLATING SYSTEM FOR BONE FIXATION AND METHOD OF IMPLANTATION

REFERENCE TO PRIORITY DOCUMENT

This application claims priority of co-pending U.S. Provisional Patent Application Ser. No. 60/533,062, entitled "Plating System for Bone Fixation and Method of Implantation", filed Dec. 29, 2003, U.S. Provisional Patent Application Ser. No. 60/551,263, entitled "Plating System for Bone Fixation and Method of Implantation, filed Mar. 8, 2004, and U.S. Provisional Patent Application Serial No. 60/603,808, entitled "Bone Fixation Plate and Method of Implantation, filed Aug. 23, 2004. Priority of the aforementioned filing dates is hereby claimed, and the disclosures of the Provisional Patent Applications indicated above are hereby incorporated by reference in their entirety.

BACKGROUND

The present disclosure is directed at skeletal plating systems, components thereof, and method of implant placement. Such systems are used to adjust, align and maintain the spatial relationship(s) of adjacent bones or bony fragments during healing and fusion. Such systems may be comprised of bone distraction devices, skeletal plates, bone screws and/or bone cables, bone screw-to-plate locking mechanisms, and any additional instruments for implant placement.

Whether for degenerative disease, traumatic disruption, infection or neoplastic invasion, surgical reconstructions of the bony skeleton are common procedures in current medical practice. Regardless of anatomical region or the specifics of the reconstructive procedure, many surgeons employ an implantable skeletal plate to adjust, align and maintain the spatial relationship(s) of adjacent bones or bony fragments during postoperative healing. These plates are generally attached to the bony elements using bone screws or similar fasteners and act to share the load and support the bone as osteosynthesis progresses.

Available plating systems used to fixate the cervical spine possess several shortcomings in both design and implantation protocols. These plates are manufactured and provided to the surgeon in a range of sizes that vary by a fixed amount. This mandates that a large number of different size plates must be made and inventoried—adding to cost for manufacturer, vendor, and end user (e.g., hospitals). More importantly, the pre-manufactured sizes may not precisely fit all patients forcing surgeons to choose between a size too small or too large.

Current cervical plates are not modular, and will not permit addition of one plate to another for extension of the bony fusion at a future date. It is accepted that fusion of a specific spinal level will increase the load on, and the rate of degeneration of, the spinal segments immediately above and below the fused level. As the number of spinal fusion operations have increased, so have the number of patients who require extension of their fusion to adjacent levels. Currently, the original plate must be removed and replaced with a longer plate in order to fixate the additional fusion segment. This surgical procedure necessitates re-dissection through the prior, scarred operative field and substantially increases the operative risk to the patient. Further, since mis-alignment of the original plate along the vertical axis of the spine is common, proper implantation of the replacement plate often requires that the new bone screws be placed in different bone holes. The empty holes that result may act as stress concentration points within the vertebral bodies, as would any empty opening or crack within a rigid structural member, and lead to bone fracture and subsequent screw/plate migration.

Current plates may provide fixation that is too rigid. Since bone re-absorption at the bone/graft interface is the first phase of bone healing, fixation that is too rigid will not permit the bone fragments to settle and re-establish adequate contact after initial bone absorption. This process is known as "stress shielding" and will lead to separation of the bony fragments and significantly reduce the likelihood of bony fusion. Unsuccessful bone fusion may lead to construct failure and will frequently necessitate surgical revision with a second operative procedure.

Benzel (U.S. Pat. Nos. 5,681,312, 5,713,900) and Foley (Pat. Applic. Pub. No. US2001/0047172A1) have independently proposed platting systems designed to accommodate bone settling. In either system, however, bony subsidence causes one end of the plate to migrate towards an adjacent, normal disc space. This is highly undesirable since, with progressive subsidence, the plate may overly the disc space immediately above or below the fused segments and unnecessarily limit movement across a normal disc space. Clearly, accommodation of bone settling at the plate's end is a sub-optimal solution.

The implantation procedures of current plates have additional shortcomings. Distraction screws are used during disc removal and subsequent bone work and these screws are removed prior to bone plate placement. The empty bone holes created by removal of the distraction screws can interfere with proper placement of the bone screws used to anchor the plate and predispose to poor plate alignment along the long axis of the spine. This is especially problematic since the surgical steps that precede plate placement will distort the anatomical landmarks required to ensure proper plate alignment, leaving the surgeons with little guidance during plate implantation. For these reasons, bone plates are frequently placed "crooked" in the vertical plane and often predispose to improper bony alignment. Correct plate placement in the vertical plane is especially important in plates intended to accommodate bony subsidence, since the plate preferentially permits movement along its long axis. Thus, when the vertical axis of the plate and that of the spine are not properly aligned, the plate will further worsen the bony alignment as the vertebral bones subside.

The empty bone holes left by the removal of the distraction screws also act as stress concentration points within the vertebral bodies, as would any empty opening or crack within a rigid structural member, and predispose them to bone fracture and subsequent screw/plate migration. Improper plate placement and bony fractures can significantly increase the likelihood of construct failure and lead to severe chronic pain, neurological injury, and the need for surgical revision with a second procedure.

Yuan et al describes a multi-segmental plate consisting of two sliding parts in U.S. Pat. No. 5,616,142. While intended to be absorbable, Yuan's design permits excessive play between the sliding component and encourage bone screw loosening. In addition, this device does not permit application and maintenance of a compressive force across the bony construct, as most surgeons prefer. Baccelli noted these deficiencies in U.S. Pat. No. 6,306,136 and proposed a rigid plate capable of maintaining bony compression. Unfortunately, the latter plate did not permit subsidence.

SUMMARY

In view of the proceeding, there is a need for an improved bone plating system and placement protocol. Described herein is a modular bone plate of adjustable length that will accommodate bone settling. The device provides ease of use, reliable bone fixation, adjustable length, modular design, and the ability to accommodate and control bone settling. The device maximizes the likelihood of proper plate placement and avoids maneuvers that weaken the vertebral bodies.

In accordance with one aspect, a modular distraction screw is used for the bone work prior to plate placement. The distraction screw is placed as the first step of surgery when all relevant landmarks are still intact. After completion of the bone work, the proximal end of the distraction screw is detached, leaving a distal segment still implanted in the vertebral bodies above and below the newly fused disc space. The plate is guided to proper position along the upper and lower vertebra by the attached distal segments. The distal segments of the distraction screws are tightened onto the plate and the plate is held stationary while bone screws are placed.

The distal segments are used to guide the bone plate into the correct placement position and serve to hold the plate stationary while the plate's bone screws are placed. Since the distraction screws were placed with intact surgical landmarks, use of the distal segments to guide the plate significantly increases the likelihood of proper plate placement. In addition, this placement method allows the distal segments of the distraction screws to serve as additional points of fixation for the plate and leaves no empty bone holes to serve as stress concentration points and further weaken the vertebral bodies.

After the plate is attached to the upper and lower vertebras, the plate is set to the desired length and the locking element is deployed. If a compressive force across the vertebral bodies is desired, compression is applied prior to deployment of the locking element. After deployment, the plate maintains the force across the vertebral bodies and permits a pre-determined amount of bony subsidence. The plate does not overlap the adjacent disc space with bone subsidence, since movement is accommodated at the level of settling bone and not at the plate's end. Moreover, the plate permits maintenance of a compression force as well as accommodation and control of bony subsidence, among other features.

Extension of the fusion at a later date is easily accomplished without plate removal. An adapter is placed at either end of the plate to permit fusion extension. The procedure is started by connecting a modified distraction screw to the coupler at the end of the plate immediately adjacent to the disc to be fused. A modular distraction screw is inserted into the adjacent vertebra and a discectomy and subsequent fusion are performed within the intervening disc space. After completion of the bone work, the modified distraction screw is removed leaving the bare coupler on the end of the plate. The proximal segment of the distraction screw is also removed leaving the distal segment attached to the adjacent vertebral body. An extension plate is used to span the space between the distal segment of the distraction screw on the adjacent vertebra and the end-coupler on the original plate. In this way, the fusion is extended and the newly fused segment is fixated without removal of the original plate.

In accordance with one aspect, there is disclosed a bone fixation device, comprising: a first member connectable to a first vertebra; a second member connectable to a second vertebra and interconnected with the first member, the first and second members being movable relative to one another; and at least one distraction screw interface configured to couple to a distraction screw for temporarily immobilizing the bone fixation device relative to the first and second vertebra, wherein the distraction screw couples to the distraction screw interface at a plurality of locations relative to the bone fixation device.

In accordance with another aspect, there is disclosed a bone fixation device for retaining bone structure in a desired spatial relationship, comprising: a first member connectable to a first bone structure; a second member connectable to a second bone structure and interconnected with the first member, wherein the first and second members are movable relative to one another across a range of motion; and a locking member that transitions between a first state wherein the locking member engages the first member, and a second state wherein the locking member engages the second member, wherein the locking member and the first member move in unison across a first distance when the locking member is in the first state, and wherein the locking member and the second member move in unison across a second distance when the locking member is in the second state.

In accordance with another aspect, there is disclosed a device for positioning a bone fixation plate relative to a bone structure, comprising: a holder portion configured to be removably attached to the bone fixation plate; and an actuator coupled to the holder portion, wherein the actuator is actuated to move the holder portion to thereby adjust the size of the bone fixation plate.

The plating systems described herein provide ease of use, reliable bone fixation, adjustable length, modular design, and the ability to accommodate and control bone settling. The plate maximizes the likelihood of proper plate placement, avoid maneuvers that weaken the vertebral bodies, and provides a significant advantage over the prior art. These and other features will become more apparent from the following description and certain modifications thereof when taken with the accompanying drawings.

BRIEF DESCRIPTION OF THE DRAWINGS

FIG. 3 shows a distal section of the distraction screw.

FIG. 4 shows components of a proximal portion of the distraction screw.

FIG. 5 shows an enlarged view of the proximal portion coupled to the distal portion of the distraction screw.

FIGS. 12A-12D shows various views of a locking component of the device.

FIGS. 14A and 14B shows a cross-sectional views of the device.

FIGS. 15A and 15B shows cross-sectional, perspective views of the device.

FIG. 19 shows a close up view of the holder interacting with the plate.

FIG. 23 shows an offset modified distraction screw in conjunction with a plate mounted on a bone structure.

DETAILED DESCRIPTION

Disclosed is a modular bone distraction screw and a plate-based bone fixation device. While they may be used in any skeletal region, these devices are well adapted for use in the spine. Exemplary embodiments of the fixation device, distraction screw and the method of use are described with respect to the spine region. The plate has adjustable length and can accommodate bone settling. The method of use for each device is described and illustrated herein.

Modular Distraction Screw

Figure 1:
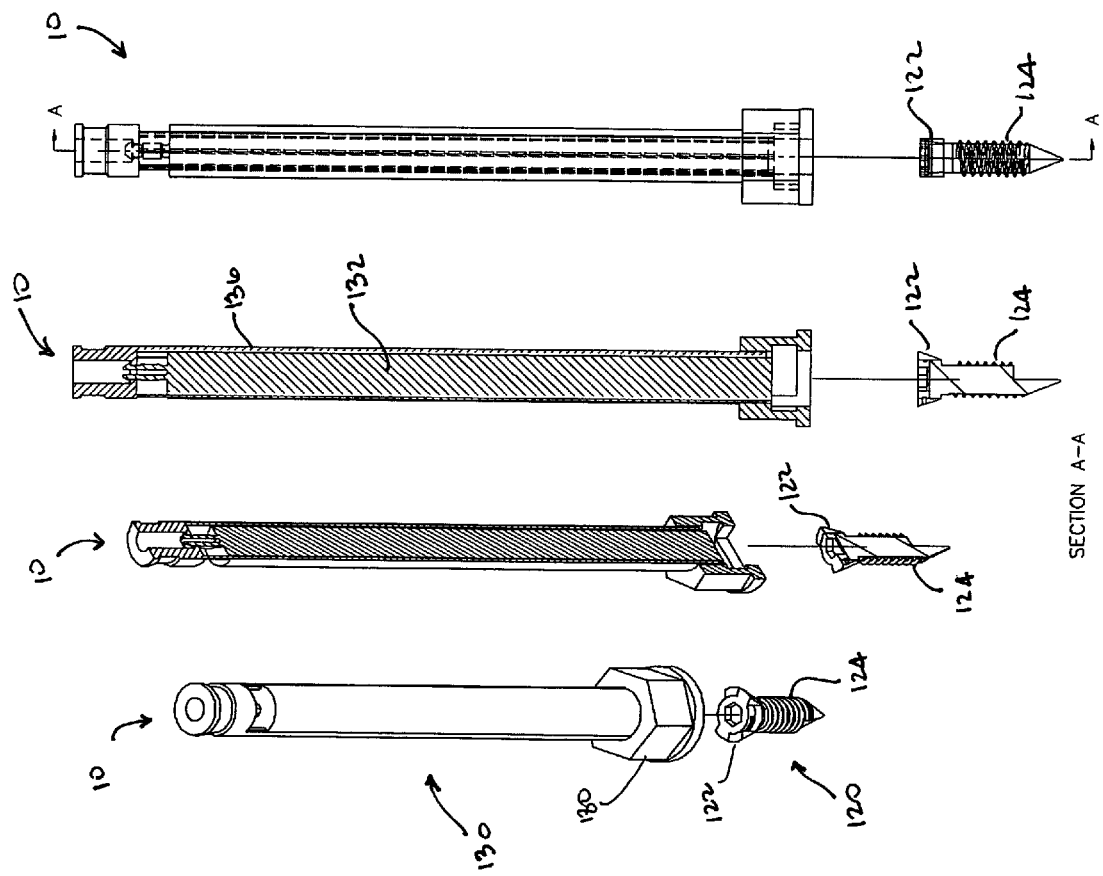
FIG. 1 shows various views of a modular distraction screw.
Figure 2:
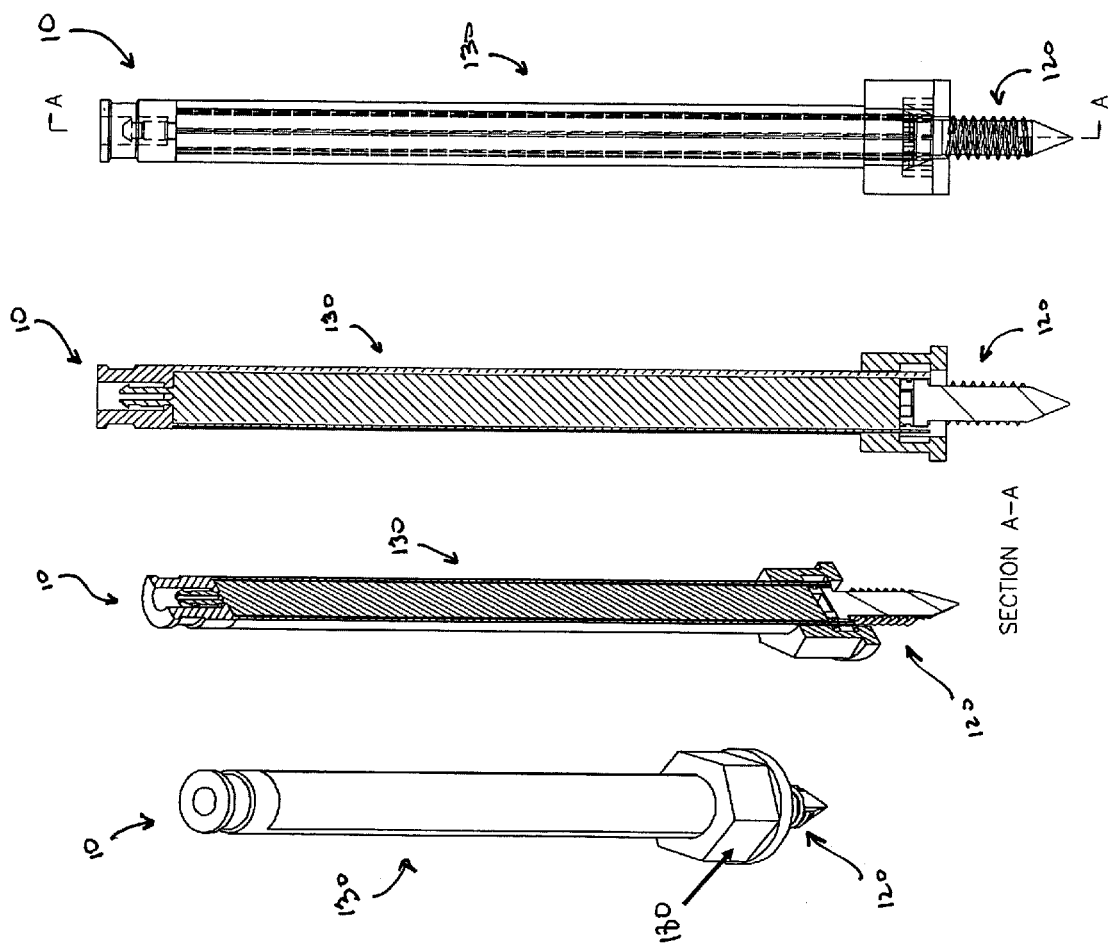
FIG. 2 shows the distraction screw in an assembled state such that a distal segment is coupled to a proximal segment.

FIG. 1 shows various views of a modular distraction screw 10, which is comprised of a distal segment 120 and a removable proximal segment 130 coupled to the distal segment 120. The distal segment 120 has a head portion 122 and a threaded shank portion 124, which can be securely fastened unto a body structure such as bone. The proximal segment 130 is comprised of an elongated body 132 that is axially positioned within a sheath-like deployable member 136. Elongated body 132 has two smooth-walled external indentations 134 and deployable member 136 is situated within those indentations. Deployable member 136 is adapted to be retractably deployed beyond the distal end of indentations 134. FIG. 2 shows the distraction screw 10 in an assembled state such that the distal segment 120 is coupled to the proximal segment 130.

FIG. 3 shows various views of distal segment 120 of the distraction screw 10. Distal segment 120 is comprised of a threaded shank portion 124 and a head portion 122. The threads can vary in configuration. For example, the threads can be self-tapping and/or self-drilling. Depending on the particular application, the shank portion 124 can be of variable lengths and diameter and the threads can be of any design that is suitable for attachment onto bone.

As shown, an embodiment of head portion 122 is composed of at least two segments, including first segment 123, which is rotationally positioned within second segment 125. The second segment 125 has two or more protrusions that limit the rotation of first segment 123. When a clockwise rotational force is applied to a central indentation 1222 within first segment 123, the first segment 123 will rotate until stopped by the interaction of protrusion 1224 and indentation 1226. Once stopped, application of additional rotation will cause distal segment 120 to exert force against the protrusions 1224, such that the entire distal segment turns in unison, such as in a clock-wise fashion. Conversely, application of a counter clock-wise rotational force will return sub-segment 1220 to the closed position and further rotation will cause distal segment 120 to turn in unison in a counter clock-wise fashion.

The proximal segment 130 is now described in more detail with reference to FIG. 4, which shows the elongated body 132 and the deployable member 136 of the proximal segment.

Figure 6:
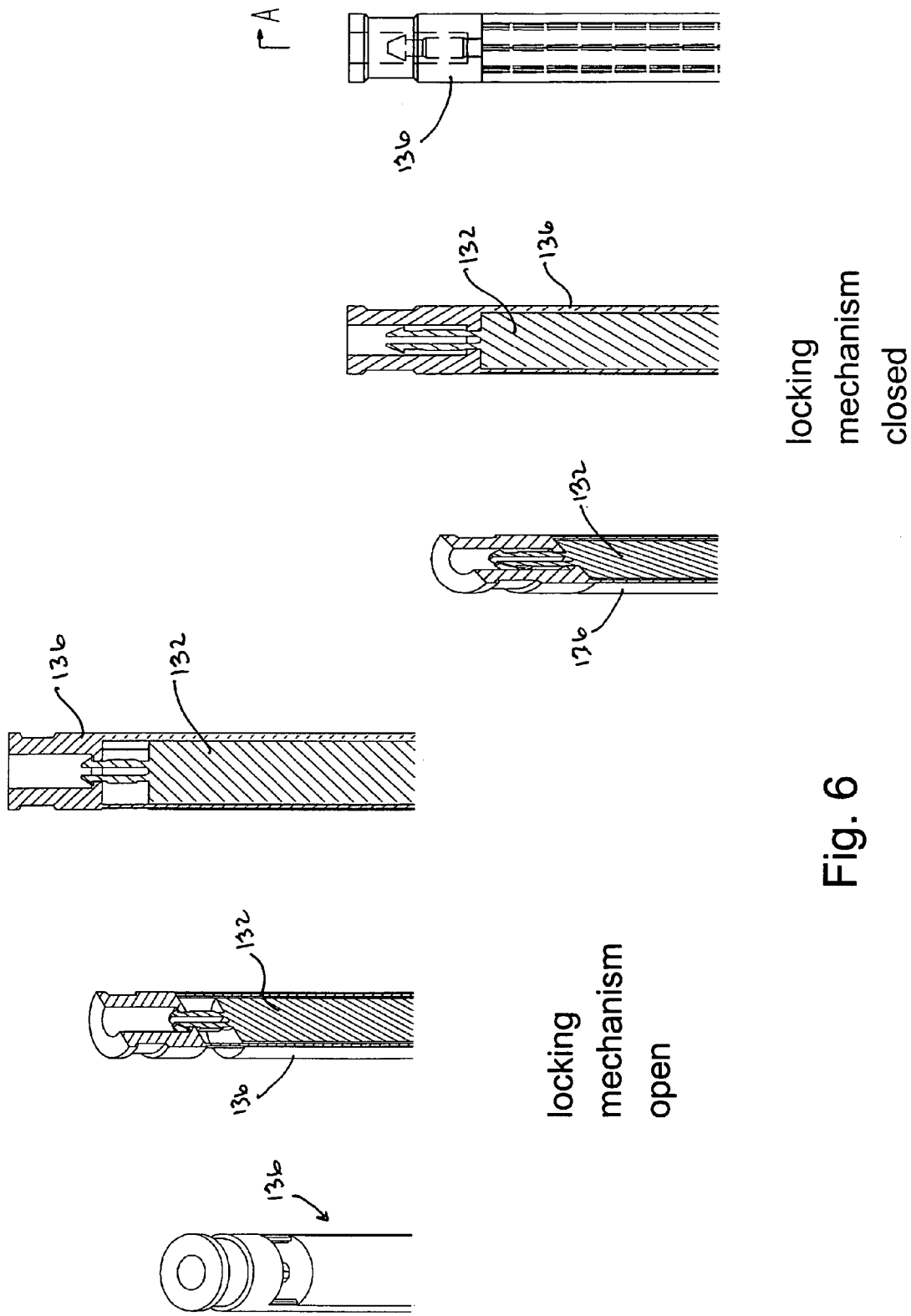
FIG. 6 shows various views of the interaction of an elongated body and a deployable member at the upper end of an assembled proximal segment of the distraction screw.
Figure 7:
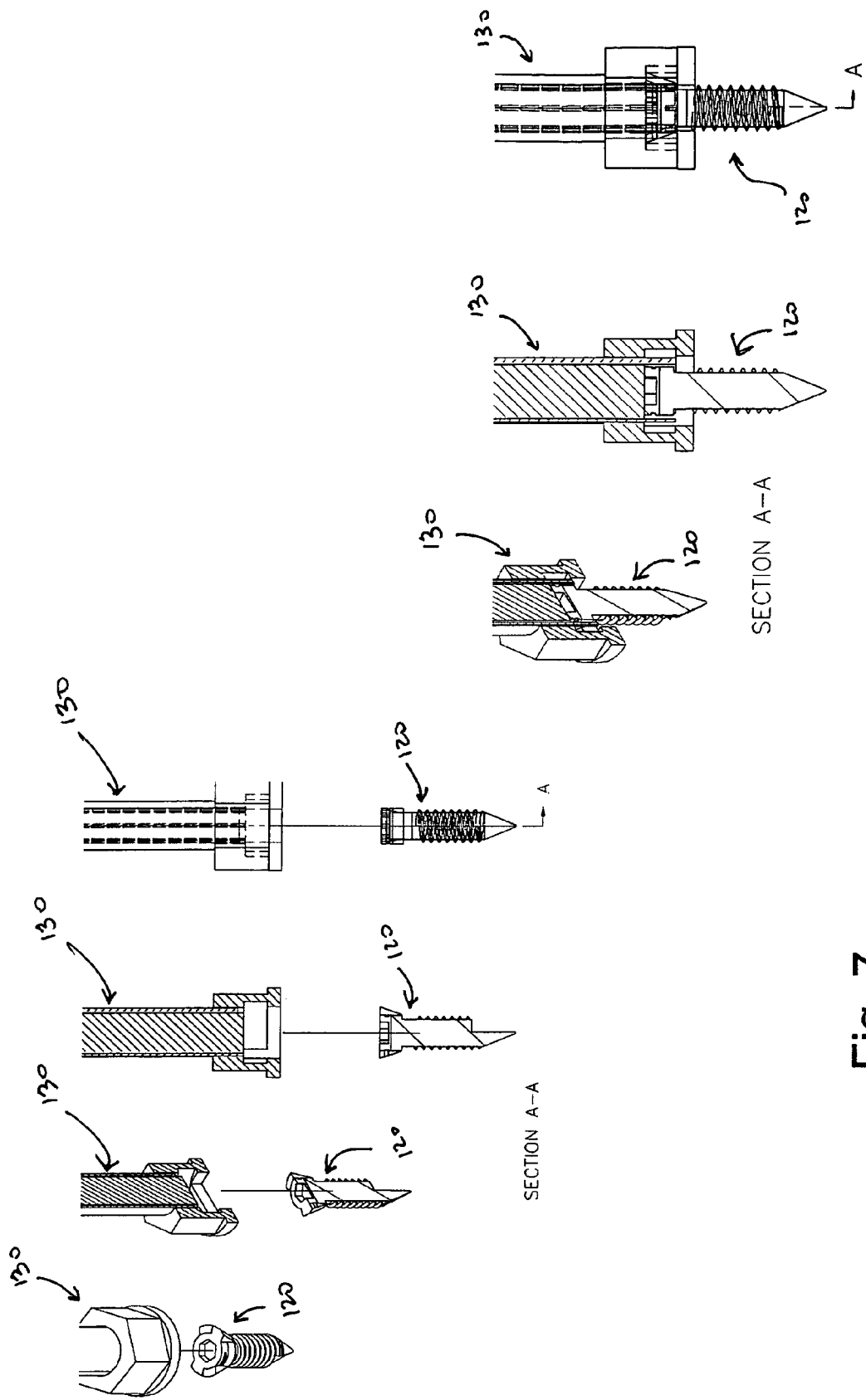
FIG. 7 illustrates how the assembled proximal segment couples to the distal segment of a distraction screw.

Upper and lower views of elongated body 132 are shown on the left of FIG. 4 and deployable member 136 is shown interacting with distal segment 120 on the right (without body 132). The deployable member has a pair of arms 501 that couple to the head portion 122 of the distal segment 120. FIG. 5 shows a close-up view of the arms 501 that permit proximal segment 130 to lock onto distal segment 120. As shown, the arms 501 are sized to couple to the head of the distal segment. FIG. 6 shows the interaction of elongated body 132 and deployable member 136 at the upper end of assembled proximal segment 130. As shown, the upper end of the elongated body 132 has a tab configuration that mates with the upper end of the deployable member 136. FIG. 7 illustrates how the assembled proximal segment 130 couples to distal segment 120.

The coupled proximal segment 130 and distal segment 120 employing the previously described means of engagement provide a modular distraction screw. When fully assembled, the screw will function as a unitary device. In a surgical application, a wrench (not shown) is attached to the distraction screw and the distraction screw is positioned at a site of a bone. A rotational force is applied to portion 180 (FIG. 1) of elongated body 132 causing the proximal and distal segments to rotate in unison so that the threads of distal segment 120 engage the underlying bone and shank 124 is advanced into the bone.

After the distraction screws are used to perform the bone work, proximal segments 130 are detached. Each distraction screw is disassembled into its components and a distal segment 120 is left attached each vertebral body. The distal segment provides enhanced structural integrity of the bone by reducing the stress concentration generally expected of an empty opening in a structural member. In addition, leaving the distal segment 120 attached to bone eliminates the robust bone bleeding encountered after removal of current, commercially-available distraction screws and obviates the need to fill the empty hole with a hemostatic agent.

Each distal segment 120 also provides an anchor point for the skeletal plate and helps insure proper plate placement. Since placement of the distraction screws is performed as the first step in the surgical procedure, the anatomical landmarks required to ensure proper alignment of the plate in the desired anatomical plane are still intact.

Plate Device

Figure 8:
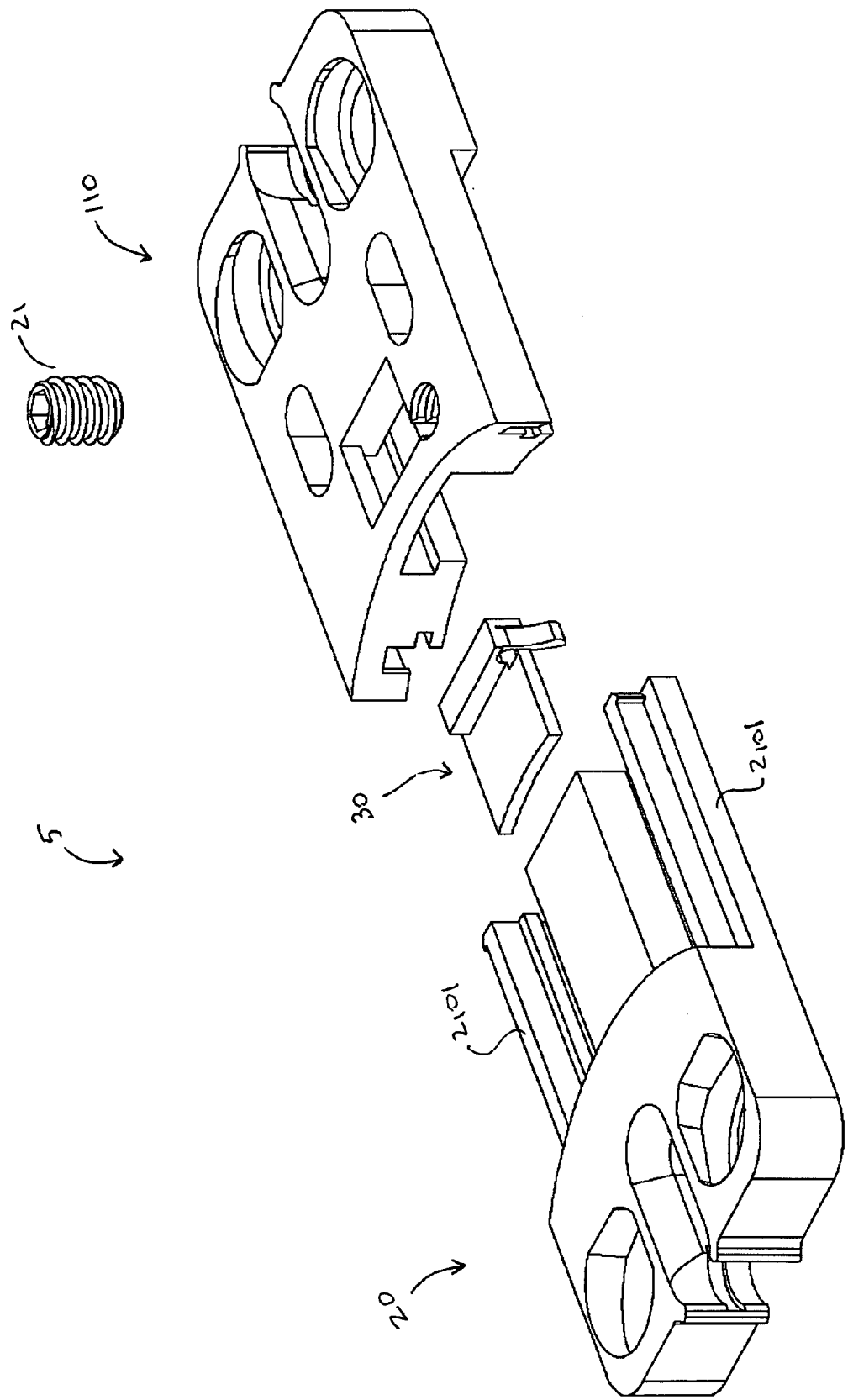
FIGS. 8 and 9 shows perspective views of a bone fixation device configured to retain bone portions such as cervical vertebra of a spinal column in a desired spatial relationship.
Figure 9:
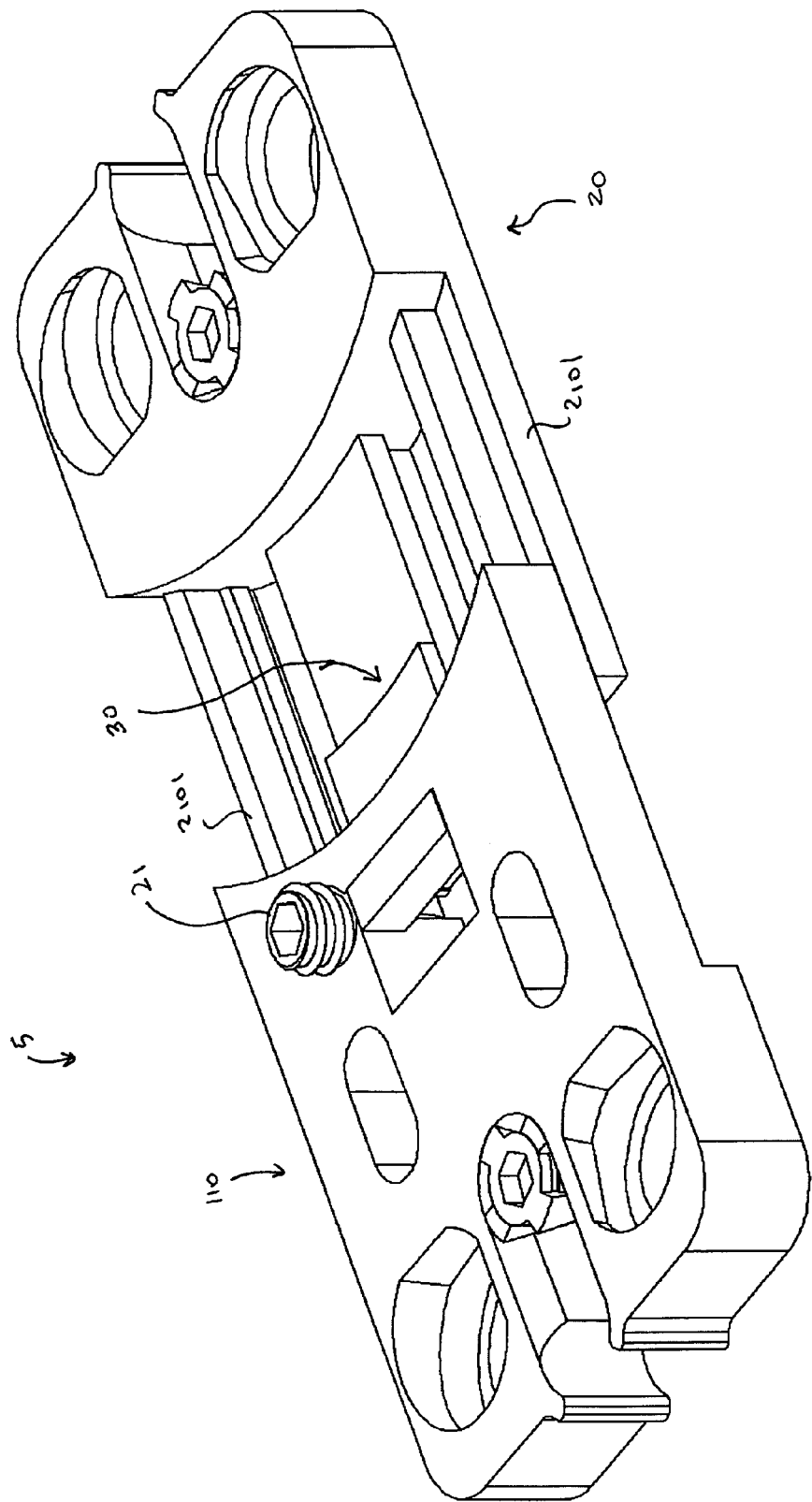

FIGS. 8 and 9 shows perspective views of a bone fixation device 5 configured to retain bone portions such as cervical vertebra of a spinal column in a desired spatial relationship. FIG. 8 shows the device 5 in an exploded state and FIG. 9 shows the device 5 in an assembled state. The device 5 is preferably convex in both the vertical and horizontal planes in order to conform to the shape of the anterior aspect of the vertebral bodies. Further, the plate surface immediately adjacent to the bone may contain one or more indentations (not shown) that permit the placement of additional curvature.

With reference to FIGS. 8 and 9, the device 5 includes a first sliding component 20, a second sliding component 110, and one or more locking components 30, which are described in more detail below. The sliding component 20 includes one or more elongate rods 2101 that extend along a longitudinal direction. The device 5 further includes a plurality of fasteners, such as bone screws, that can be used to fasten the sliding component 20 and sliding component 110 to a bone such as to a cervical vertebrae. The bone screws may be of any known design that is appropriate for fixation of and implantation into human bone.

After engaging the underlying bone, the screws may be further attached to the plate using any of a variety of screw-to-plate locking mechanisms. Such mechanisms include, but are not limited to, the methods and devices illustrated in U.S. Pat. Nos. D440311S, D449692S, 5,364,399, 554,612, 5,578,034, 5,676,666, 5,681,311, 5,735,853, 5,954,722, 6,039,740, 6,152,927, 6,224,602, 6,235,034, 6,331,179, 6,454,769, 6,599,290, 6,602,255, 6,602,256, 6,626,907, 6,652,525, 6,663,632, and 6,695,846. It is understood that one of ordinary skill in the art can apply these or any other suitable screw retention system and method to the plate devices described herein.

The components 20 and 30 are configured to slidingly move relative to one another. In one embodiment, the component 110 slides along elongate rods 2101 that extend from the sliding component 20 such that the component 110 can slide along a span, or degree, of linear movement. Alternately, the rods 2101 can have a curvature to provide a curved range of movement. It should be appreciated that the rods 2101 can have a variety of cross-sectional shapes. For example, the rods 2101 are shown having a straight-lined cross-sectional shape, although the cross-sectional shape can be circular or oval.

The third component 40 can be manipulated to control the degree of movement that is allowed between the components 20 and 30. As described below, the third component 40 can transition between two or more states that control the range of motion of the first component relative to the second component. An actuation member comprising a screw 21 can be coupled to the component 110 and the component 40 to transition the component 40 between the two states. When the locking component is in an open, or unlocked, state, the first and second components can move across a first range of motion relative to one another. When the adjustor component is in a closed, or locked, state, the first and second components can move across a second range of motion relative to one another. In one embodiment, the "range of motion" comprises linear and sliding movement that spans a predetermined distance. The linear movement can be in the longitudinal direction, which corresponds to the longitudinal axis of the spinal column. In one embodiment, the range of motion is a non-zero value both when the component 40 is in the unlocked or locked state. However, it should be appreciated that the range of motion does not have to be a non-zero value.

Each of the components 20 and 30 of the device 5 includes at least one bone screw interface, such as one or more boreholes, that can receive or that can matingly engage with a distraction screw, as described below. The borehole permits an additional distraction screw to be attached to the underlying vertebra and/or the device 5 without removing the device 5 from the vertebra.

The device 5 includes a modular aspect that permits the device 5 to be modularly attached to a second device, such as, for example, a coupler to a second bone fixation device, while the device 5 is attached to a spine. The device 5 does not have to be removed from the spine in order to modularly attach the second device to the device 5 in a modular fashion. It should be appreciated that the second device can be a device other than a bone fixation device. When the second device is coupled to a bone fixation device, the modular attachability allows a bone graft to be extended to additional vertebrae without having to remove the original bone fixation device.

FIGS. 10A-10E illustrates various views of sliding component 110, which has two boreholes 1110 which are angled towards each other in the horizontal plane and away from the sliding end in the vertical plane. The boreholes 110 are configured to receive a bone screw that can be used to attach the component 110 to an underlying bone structure. A depression 1120 is present between boreholes 1110 with an elongated channel 1130 within that depression. A wall is situated between the top of channel 1130 and the opening of depression 1120. The wall is angled relative to the horizontal plane.

The channel 1130 is configured to receive a distraction screw, such as, for example, the modular distractions screw described herein or other type of distraction screw. Advantageously, the channel 1130 is shaped such that the distraction screw can be positioned at various locations along the channel 1130, thereby permitting a variable distance between the distraction screw and the bone screws positioned in the boreholes 110. Thus, if the distraction screw is used to immobilize the plate during bone screw placement, the position of the plate prior to bone screw placement can be adjusted by moving the plate relative to the distraction screw.

Some existing bone fixation plates have an indentation along the plate border and use conventional, non-modular distraction screws to immobilize the plate during bone screw placement. Since the distraction screws make contact with the plate at fixed region of the plate, the distraction screws can only fixate the plate when they're tightly fitted against it. This mandates that the bone screw center must be placed a constant distance from the center of the distraction screw in the vertical plane.

A fixed spatial relationship between the bone screw and distraction screw is highly undesirable. Since bone spur formation obscures the true position of the vertebral end plate at the time of distraction screw placement, bone screw placement that is based on the position of the distraction screw will significantly increase the likelihood of improper plate placement.

In order to ensure proper plate placement, the surgeon must be able to adjustment the plate's position in the vertical plane. In the devices described herein, after the optimum position is selected, the distraction screws can be used to immobilize the plate and the bone screws is then placed. This strategy is most effectively accomplished by using a slot between the bone screw holes as in the current device.

With reference still to FIGS. 10A-10E, the component 110 includes a sliding mechanism comprising a pair of longitudinally-extending rod shafts 355 that extend through the component 110. The rod shafts 355 are sized to receive a corresponding rod 2101 of the component 20, as described below. In this regard, each of the rod shafts 355 is positioned so as to be axially aligned with the corresponding pair of rods 2101 of the component 20 and has a shape configured to receive a respective rod shaft. In one embodiment, the rods 2101 are configured to engage with the component 30 in a manner that minimizes the likelihood of the rods 2101 disengaging therefrom. In this regard, the end portions of the rods can have a size that is slightly larger than the entry diameter of the rod shafts 355 so that once the rods 2101 are positioned in the rod shafts, the enlarged diameter prevents the rods 2101 from inadvertently moving out of the shafts.

Figure 10:
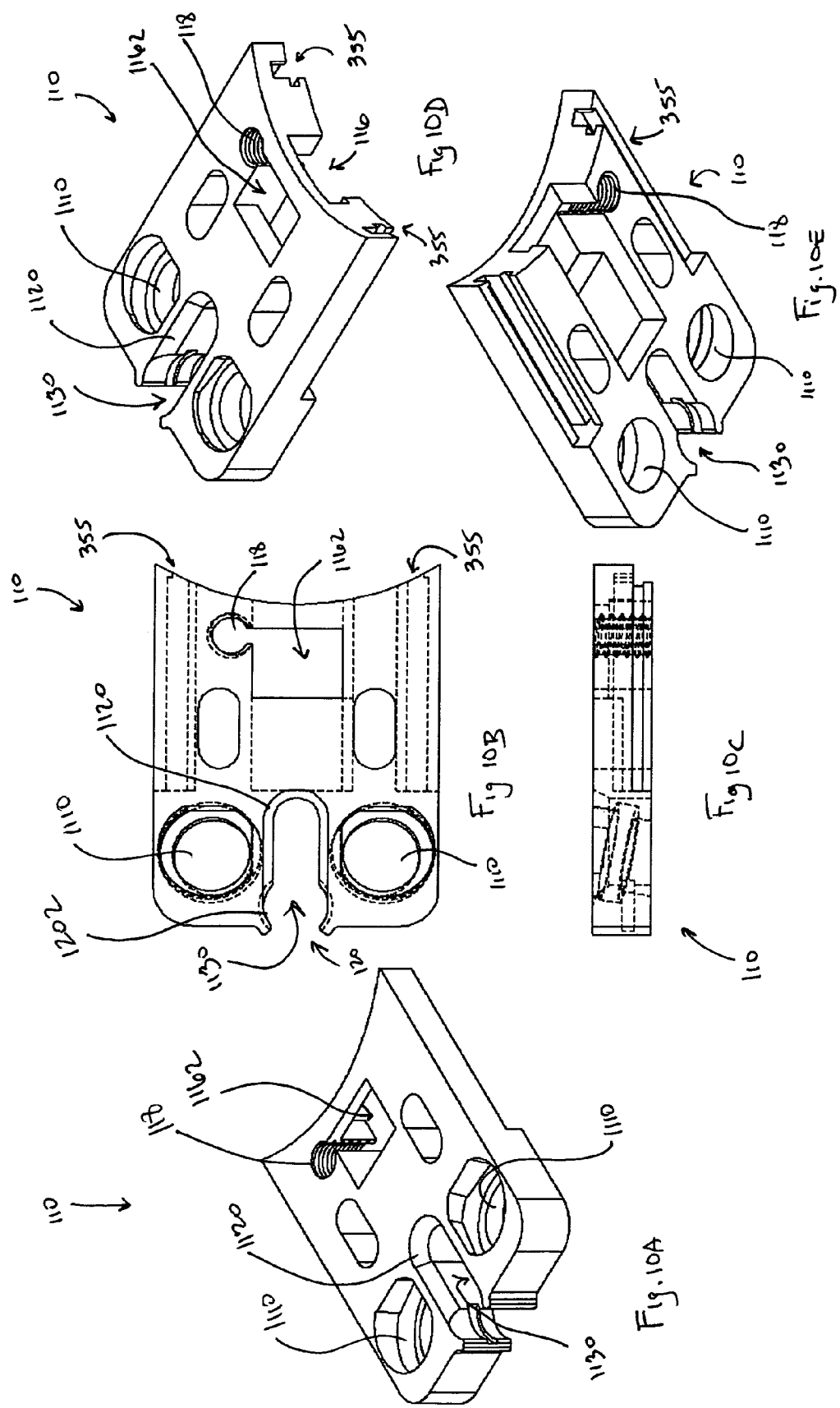
FIGS. 10A-10E illustrates various views of a sliding component of the device.
Figure 11:
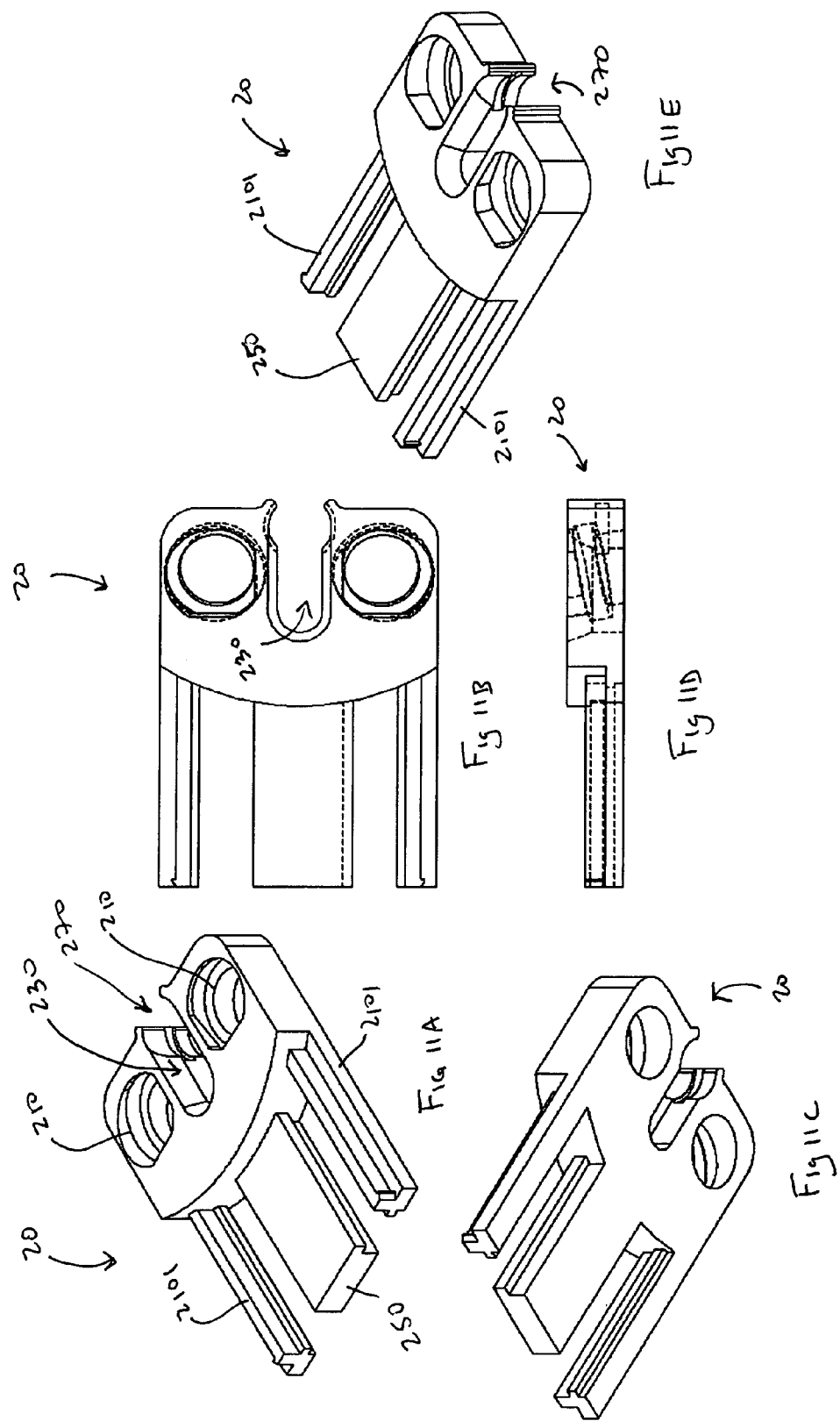
FIGS. 11A-11E illustrate various view of another sliding component of the device that couples to the sliding component shown in FIGS. 10A-10E.

The component 110 includes a central shaft or indentation 116 (FIG. 10D). An opening 1162 is situated within the top surface of indentation 116. A vertical hole 118 has threads, rests next to central indentation 116 and opens onto indentation 116 through an opening. The hole 118 is sized to receive the screw 21.

The end opposite to the sliding mechanism has an end-coupler 120 with a central hole 1202. A relief is cut along a wall of the hole 1202 to aid in the attached of any add-on devices. While depicted as a circumferential channel, the relief may be of any appropriate geometric shape that complements the add-on device. Further, the inside wall of hole 1202 may contain additional indentations, spines or texture to increase frictional contact between the plate and add-on devices.

FIGS. 11A-11E illustrate the complementary sliding component 20. Again, two boreholes 210 are present and angled towards each other in the horizontal plane and away from the sliding end in the vertical plane. Each of the boreholes 210 is sized to receive a corresponding fastener screw. In one embodiment, a screw head engagement structure, such as an annular lip or shelf, is located within each borehole 210. The head of a fastener screw can engage the shelf and provide a fastening force thereto during fastening of the component 20 to a vertebra. In the illustrated embodiment, the component 20 has two boreholes 210, each located near a transverse side of the main body. The boreholes 210 can be aligned with an axis that is oriented in the true vertical plane, or the axis can form an angle with the vertical. For use in the cervical spine, boreholes 210 can be angled towards each other in the horizontal plane and away from the rods 2101 in the vertical plane. The top opening of the boreholes 210 may be flush with the outer surface, can be curved, or can be further recessed so as to form the shelf 315.

A depression is present between the boreholes 210 with an elongated channel 210 positioned between the boreholes 210. A wall is situated between the top of channel 230 and depression 220 and it is angled with the true vertical.

As mentioned, the sliding end of component 20 includes a pair of rods 2101 and a central projection 250. The rods 2101 are sized to be inserted into the channels 355 in the component 110 and the central projection is sized to be inserted into the indentation 116. The ends of the rods 2101 have additional projections that lock the plate together so that once assembled it can not be pulled into its individual components. Likewise, the central projection 250 complements with indentation 116 of component 110. An end coupler 270 is located at the an opposite end of component 20 and may contain additional indentations, spines and texture- as described for end-coupler 120.

FIGS. 12A-12D illustrates various views of the locking element 30. The locking element includes a plate portion 1181 that is sized and shaped to be received into the indentation 116 along with the central projection 250 of the component 20. A raised region 1183 protrudes into the opening 1162 in the component 20 when the device is assembled. The locking element 30 further includes a retractable side-arm 320. The side-arm 320 fits within opening 1182 of component 110 and an inner aspect of arm 320 is preferentially textured or slotted to increase fictional contact with other segments. That is, the side-arm 320 extends through the opening 1182 in the side of the hole 118 of the component 110 when the device 5 is assembled.

Figure 13:
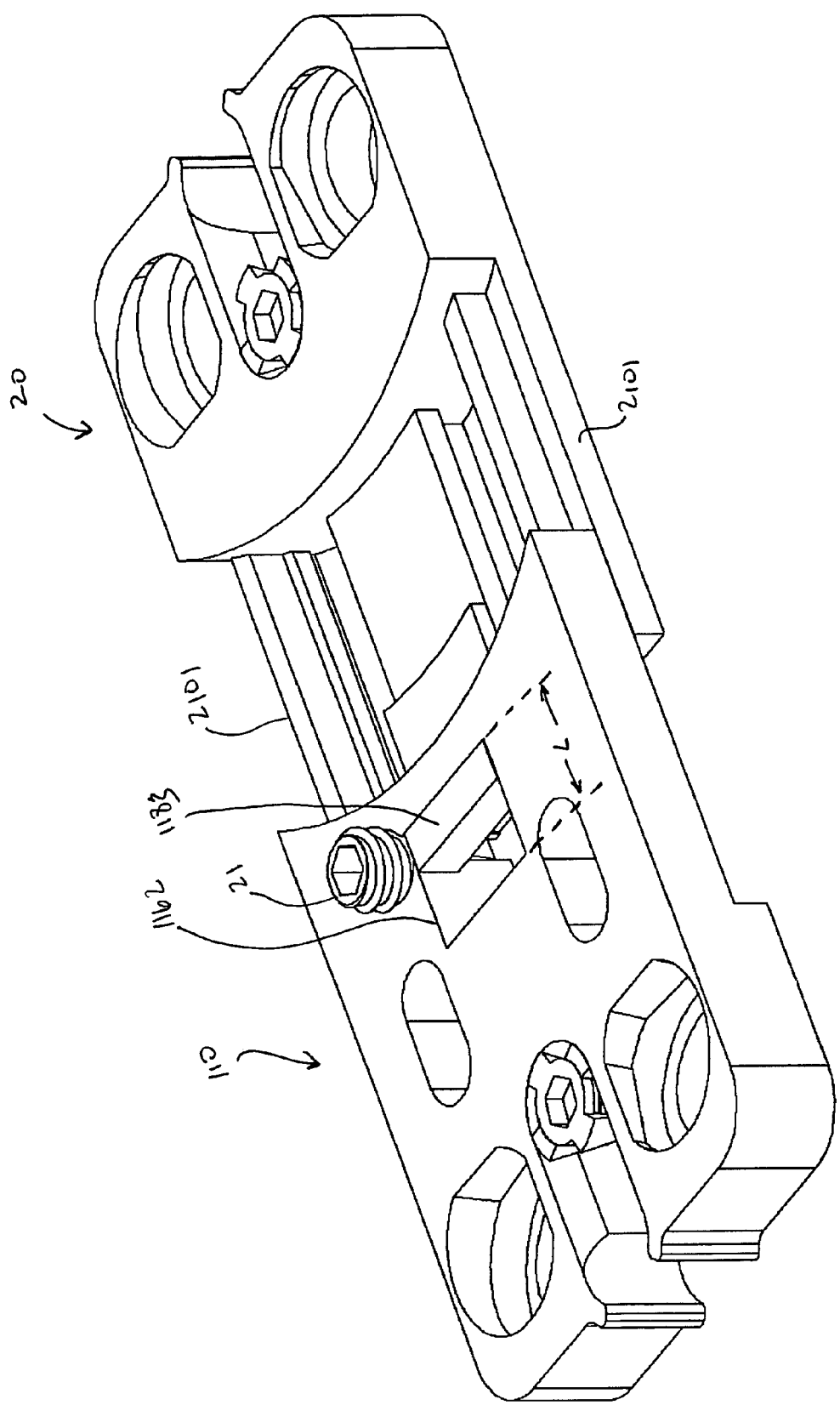
FIG. 13 shows the device in an assembled state.

FIG. 13 shows the device 5 in an assembled state. The rods 2101 of component 20 are slidingly coupled to the component 110. The locking element 30 is positioned between the components 20 and 110 such that the raised region 1183 protrudes through the opening 1162. The raised region 1183 can slide within the opening 1162 along a distance L.

The screw 21 can be moved between an open and closed state to transition the side-arm 320 of the locking element between an open state and a closed state. When the side arm is in the open state, the locking component 30 and the component 20 cannot move relative to one another, but rather move as a unitary component.

This is described in more detail with reference to FIGS. 14A, 14B, 15A, and 15B. FIGS. 14A and 15A shows the screw 21 and the locking element 30 in an open state. With screw 21 open, side-arm 320 sits within opening 1182. The side arm 320 thereby engages the component 110 so that locking element 30 and component 110 can not move relative to one another. However, component 20 can slide freely relative to element 30 and component 110 along the length of the rods 2101.

However, when screw 21 is locked and fully seated within hole 118 (as shown in FIGS. 14B and 15B), the screw 21 pushes the side-arm 320 out of the opening 1182. This causes the interior aspect of the side arm 320 to engage the projection 250. As mentioned, the side arm 320 can have a textured surface that makes contact with the side of projection 250 of component 20. Thus, with screw 21 locked, the side arm 320 of the locking component 30 engages the projection 250 of component 20 and both pieces (components 20 and 30) move in unison within opening 1162 of component 110. The extent of such movement is limited by the length L (FIG. 13) of opening 1162. In this way, when screw 21 is open, component 110 and locking element 30 move in unison relative to component 20 and provide a plate of variable length. With screw 21 closed, component 20 and locking element 30 move in unison within opening 1162 of component 110 permitting accommodation of bone subsidence.

Placement Protocol

Modular distraction screws are placed into the vertebral bodies above and below the disc to be removed as previously described. A discectomy is performed and the evacuated disc space is fused. After the bone work is complete, the screws are disassembled leaving the distal segments attached to the vertebral bodies. The distance between the distal segments is measured and a plate of appropriate size is selected. Since a sliding plate can accommodate a range of sizes, choosing the correct plate size is simplified when a sliding plate design is used.

While the preferred method of plate placement utilizes modular distraction screws, the plate may be also implanted without them. For example, a conventional one-piece distraction can be used to distract the vertebra during discectomy. After the bone work is finished, the conventional distraction screw is removed. Distal segments 120 are placed into the vertebral bodies and provide anchor points for the skeletal plate. As discussed, the plates have channels that interface with the distraction screw along a plurality of locations such that the relative positions between the distraction screws and the bone screws can be varied during placement. Alternatively, the plate may be manually held stationary while the bone screws are placed.

Figure 16:
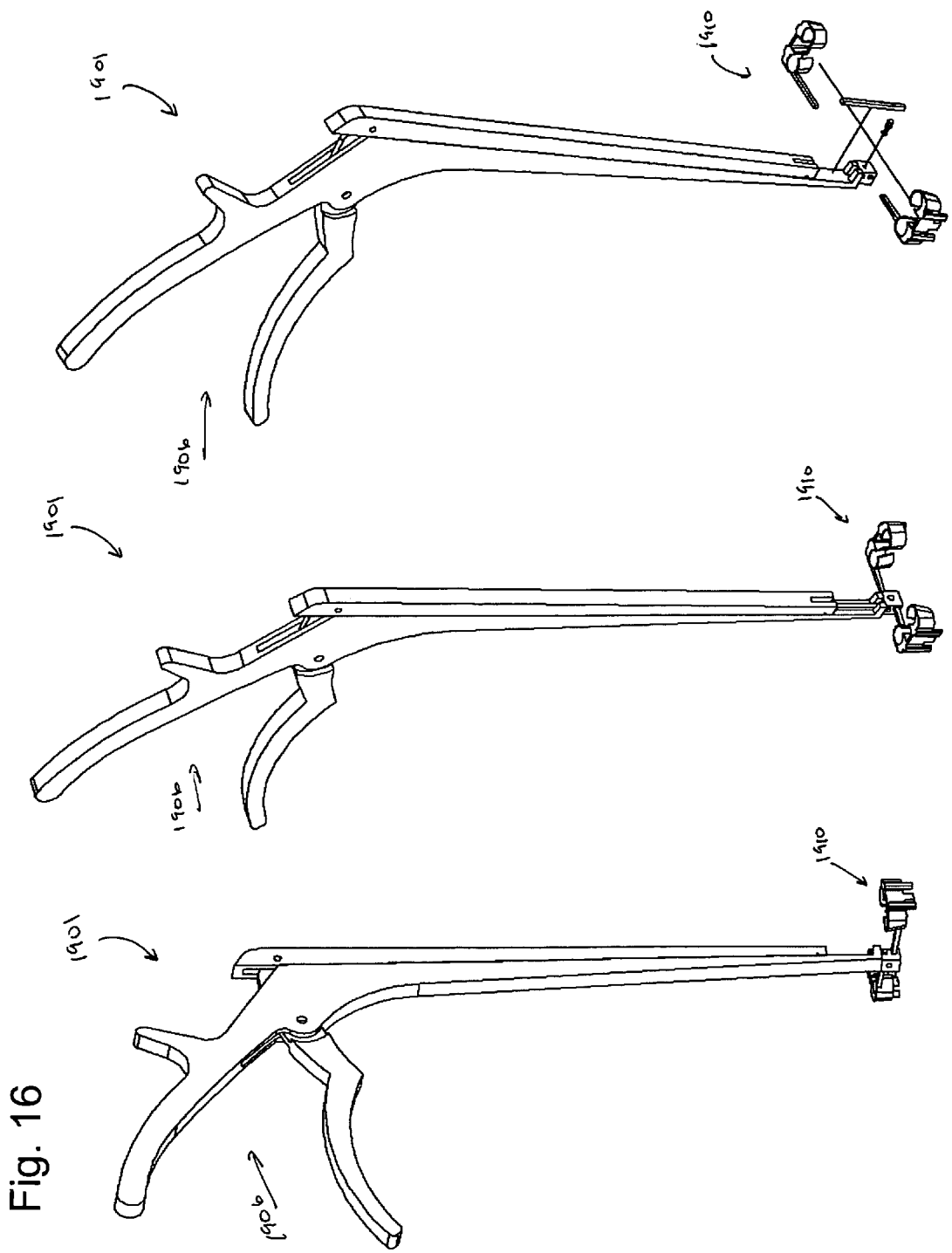
FIG. 16 illustrates an instrument used to hold a plate and guide it into position.
Figure 17:
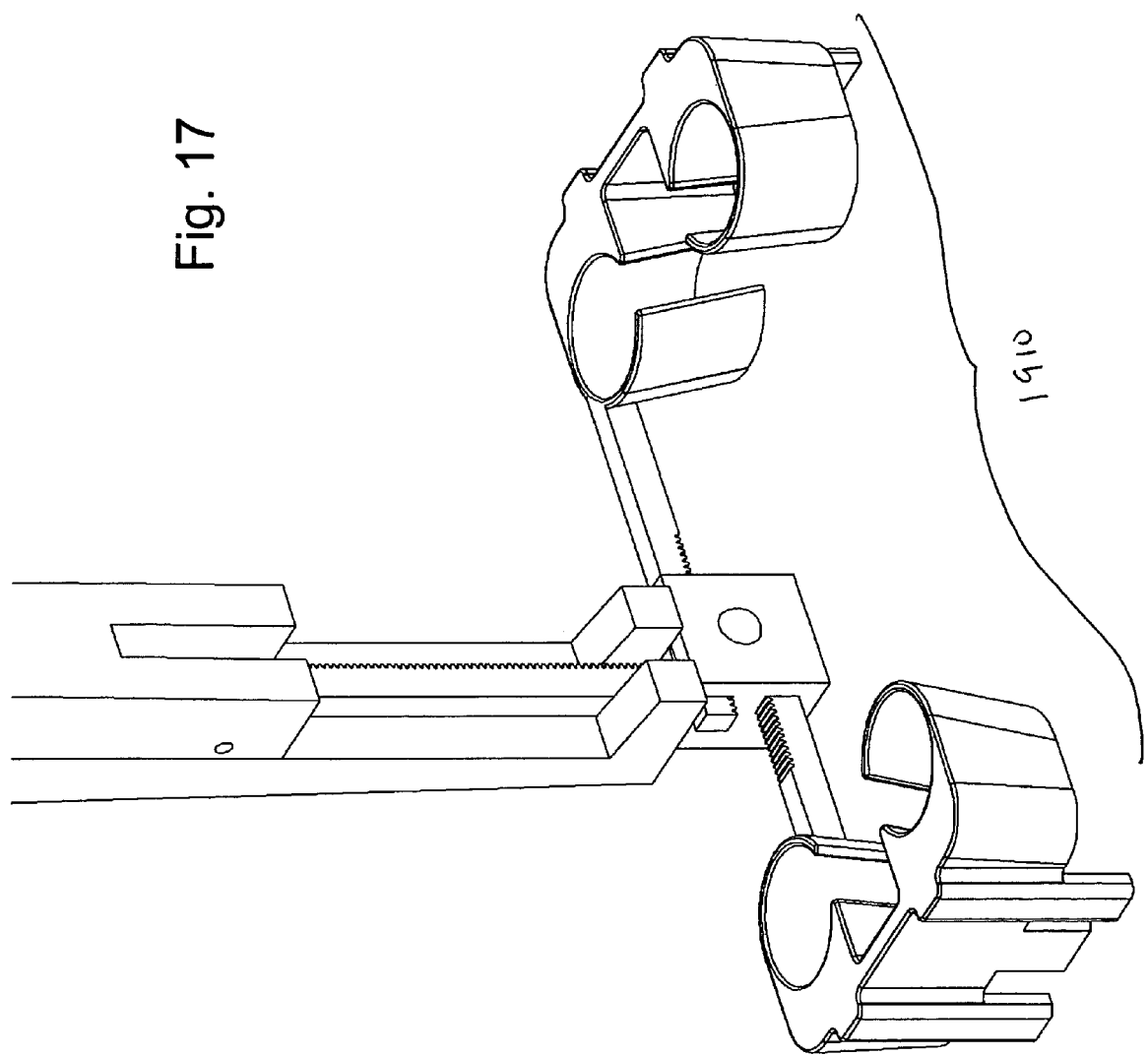
FIG. 17 shows a close-up view of the end of the instrument used to interact with the plate.
Figure 18:
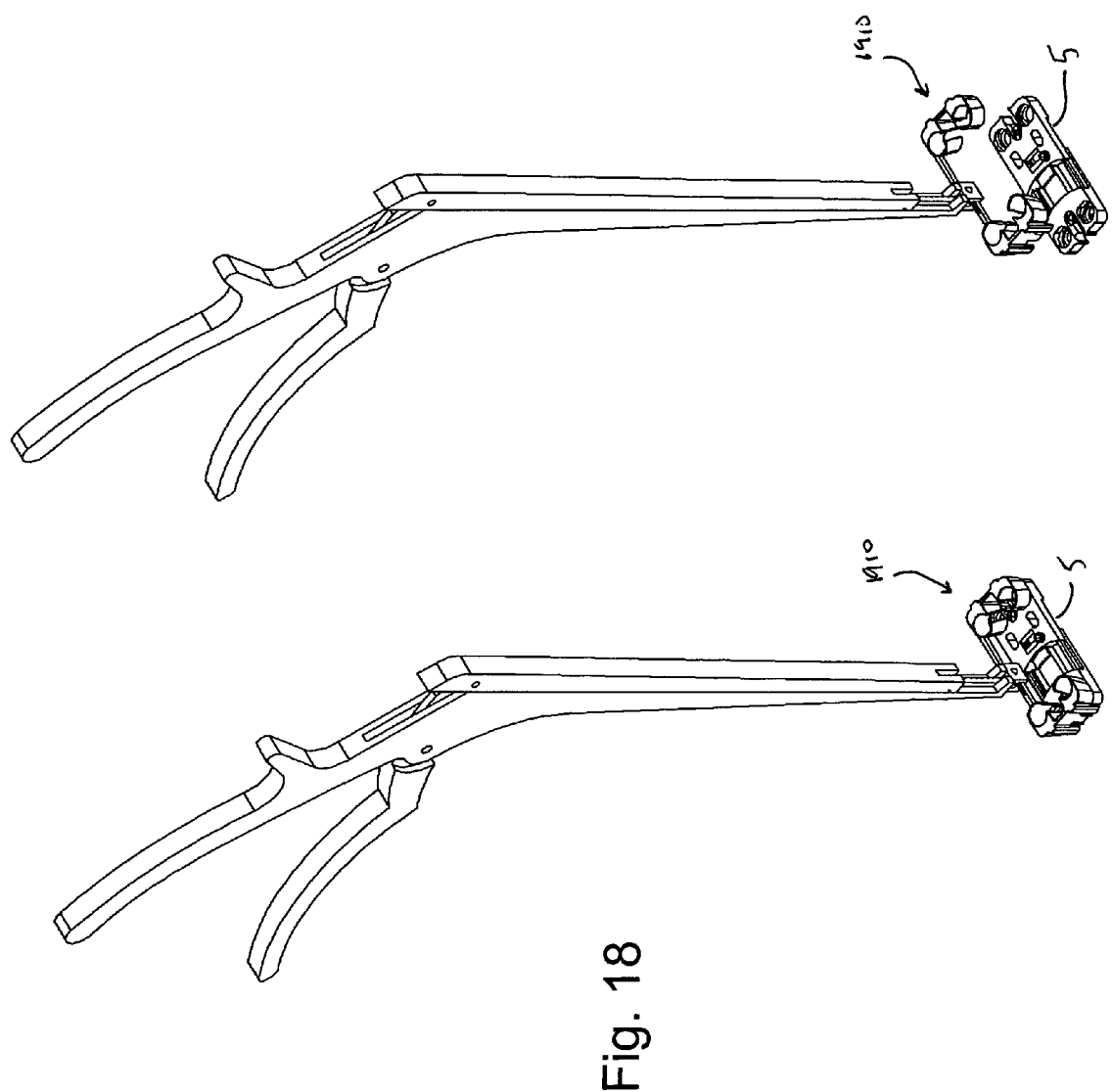
FIG. 18 illustrates the holder coupled to and interacting with the plate.

FIG. 16 illustrates a holder instrument used to hold the plate and guide it into position. FIG. 17 shows a close-up view of the end of the instrument used to interact with the plate. The holder instrument includes a holder member that is configured to couple to the plate. In particular, the holder portion includes a first attachment member that removably attaches to the first component and a second attachment member that removable attaches to the second component of the plate device. In one embodiment, the attachment members are sized and shaped to be inserted into a portion of the respective components, such as into the boreholes. FIG. 18 illustrates the holder coupled to and interacting with the plate. FIG. 19 shows a close up view of the holder interacting with the plate.

With movement of the holder's handle, the plate opens and closes. In particular, the holder 1901 has an actuator handle 1906 and a holder member 1910 (previously described) that couples to the plate device 5. The actuator handle 1906 is actuated to cause the first and second attachment members to move relative to one another. In this manner, the actuator handle 1906 can be actuated to move the first and second members relative to one another and thereby adjust the size of the device. In one embodiment, the actuator handle can be actuated using a single hand, thereby freeing the other hand for other tasks. A rack and pinion configuration can be employed to transfer movement of the handle to the attachment members of the holder. However, it should be appreciated that other mechanisms can be used.

Figure 20:
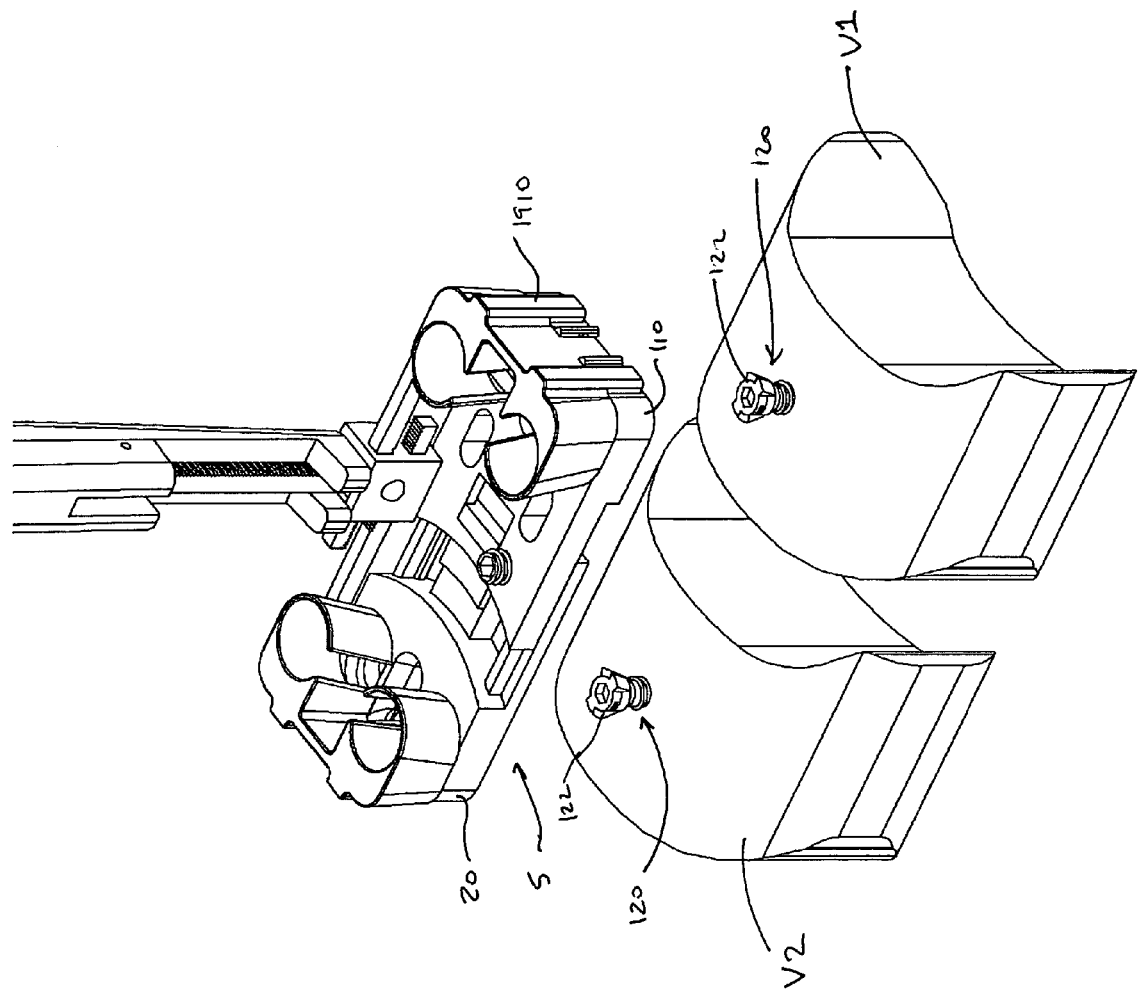
FIG. 20 shows the holder being used to deliver a plate onto a bone structure.
Figure 21:
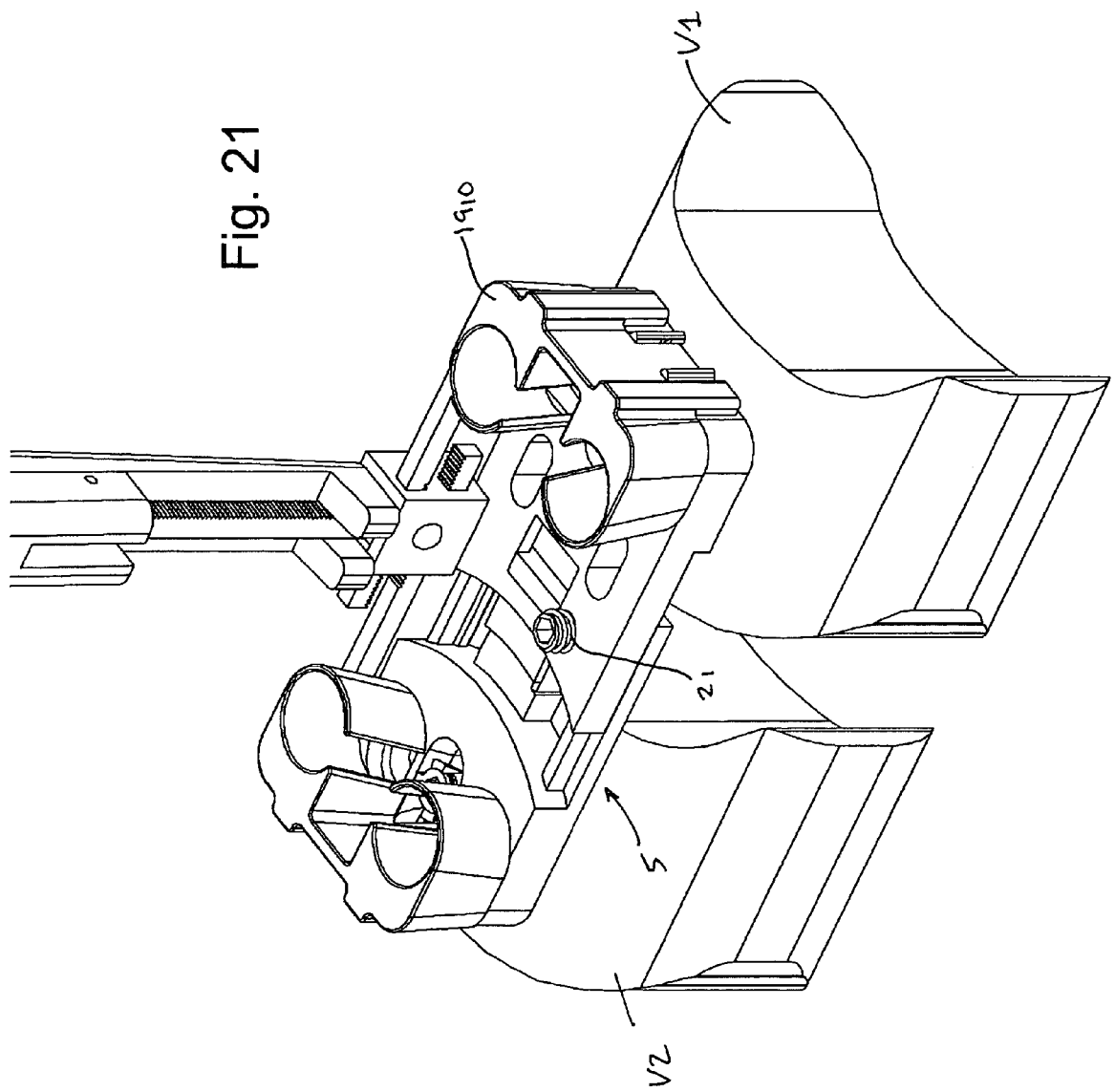
FIG. 21 shows a plate seated on a bone structure with the plate holder attached.

FIG. 20 shows the holder instrument being used to deliver a plate onto a bone structure. As illustrated in FIG. 20, the plate 5 is brought into the wound and component 110 is guided onto head 122 of distal segment 120 of the modular distraction screw anchored in one vertebra V1. The other end of the plate 5 is guided onto the distal segment 120 anchored in the other vertebra V2 component 20 is lowered onto it. FIG. 21 shows plate seated on the bone structure with plate holder 1910 attached. At this point, the plate's boreholes 110 are moved (relative to the vertebral bodies V1, V2) into optimal position for bone screw placement. After positioning the plate, a screw driver is used to turn distal segment 120 clockwise, thereby opening the head of the distal segment. Additional turns of the screw will drive the distal segment further into the bone and hold the plate between the screw head and the underlying bone.

With both distal segments locked, the plate is held stationary and the bone screws are easily placed into the underlying bone. Note that the segment of the holder adjacent to the plate's bore holes will also serve as guide for proper screw (and drill, for non-self drilling screws) placement. Bone screws and plate-to-screw locking mechanisms of any appropriate design may be employed. Compression may be added across the construct using plate holder. Screw 21 is closed thereby locking plate at the set length and maintaining any compression provided. At this point, components 20 and 110 can still move towards each other, permitting accommodation of bone settling. As mentioned, the extent of subsidence permitted is governed by the length of opening 1162.

Figure 22:
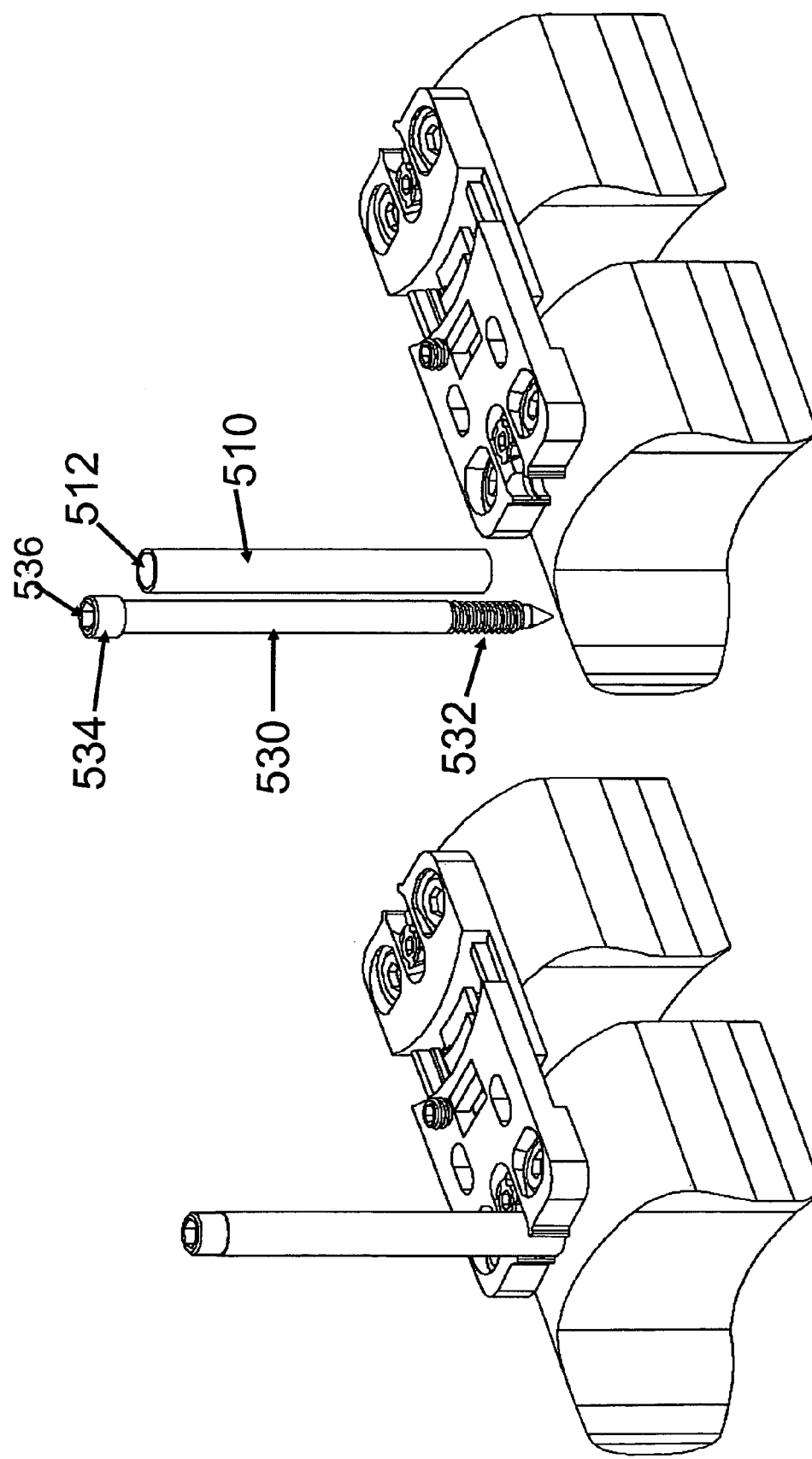
FIG. 22 shows a modular distraction screw engaging an end-coupler of a plate mounted on a bone structure.

Extension of the fusion at a future date can be accomplished without plate removal. Incorporation of the vertebral body immediately above or below into the fusion mass is started by placement of a modular distraction screw into the adjacent vertebra. A modified distraction screw is used to engage the end-coupler of the existing plate as shown in FIG. 22. The modified distraction screw is formed by an elongated body 510 with an internal bore 512 extending through its entire length. The elongated body 510 houses a deployable member 530, which is disposed within the internal bore 512. Threads 532 are located on one end of member 530 and head 534 is located on the other end. A depression 536 is formed within head 534 so as to permit engagement and rotation of deployable member 530 with a complimentary screwdriver.

When the discectomy and subsequent bone work are finished, the modular distraction screw is separated leaving the distal segment attached to vertebral body. The modified distraction screw is removed. A separate plate is used to span the distance between the distal segment 120 attached to the adjacent vertebra and the end coupler of the plate. In this way, the fusion is extended to an adjacent level without removal of the existing plate.

Occasionally, the end coupler of the plate abuts the adjacent disc space such that placement of the modified distraction screw onto the coupler hinders surgical access to the disc space. FIG. 23 shows an offset modified distraction screw which may be used in this setting. The screw components are similar to those described above for the non-offset screw.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. A bone fixation device for retaining bone structure in a desired spatial relationship, comprising:
    a first member connectable to a first bone structure;
    a second member connectable to a second bone structure and interconnected with the first member, wherein the first and second members are movable relative to one another across a range of motion;
    a locking member that transitions between a first state wherein the locking member engages the first member, and a second state wherein the locking member engages the second member, wherein the locking member and the first member move in unison relative to the second member across a first distance when the locking member is in the first state and the first and second members are each connected to a bone structure, and wherein the locking member and the second member move in unison relative to the first member across a second distance when the locking member is in the second state during use of the device.

2. A device as in claim 1, wherein at least a portion of the locking member protrudes through a hole in the first member when the locking member is in the first state.

3. A device as in claim 1, wherein at least a portion of the locking member abuts the second member when the locking member is in the first state.

4. A device as in claim 1, further comprising an actuation member that is actuated to transition the locking member between the first state and the second state.

5. A device as in claim 4, wherein the actuation member comprises a screw, wherein the locking member is in the first state when the screw is open and in the second state when the screw is closed.

6. A device as in claim 1, wherein the first distance is greater than the second distance.

7. A device as in claim 1, further comprising at least one elongate rod interconnecting the first member and the second member.

8. A device as in claim 1, wherein the range of motion is linear.

9. A device as in claim 1, wherein the first member includes a distraction screw coupler that permits the first member or the first bone structure to be coupled to a distraction screw while the first member is connected to the first vertebra.

10. A device as in claim 1, wherein the first member includes a modular coupler that can mate with a second bone fixation device.

11. A bone fixation device, comprising:
    a first member connectable to a first vertebra and containing at least one borehole configured to receive a bone anchor that attaches to the first vertebra, the first member having an inferior surface that abuts the first vertebra and an opposed superior surface;
    a second member connectable to a second vertebra and interconnected with the first member, the first and second members being movable relative to one another, the second member containing at least one borehole configured to receive a bone anchor that attaches to the second vertebra, the second member having an inferior surface that abuts the second vertebra and an opposed superior surface;
    a distraction screw and at least one distraction screw interface configured to couple to a distraction screw for temporarily immobilizing the bone fixation device relative to the first and second vertebra, the distraction screw interface comprising a slot of fixed size and shape that extends through the first member, the slot positioned at an edge of the first member such that an end of the slot is open at the edge of the first member that is positioned at the greatest distance from the second member, wherein the distraction screw is separate from a locking mechanism used to fixate the first and second members to one another, and wherein the distraction screw is adapted to fixate onto the first vertebra so as to transmit a force that displaces the first vertebra relative to an adjacent vertebra;

in a first state, the distraction screw interacts with the distraction screw interface in a manner that permits sliding movement of the distraction screw relative to the distraction screw interface along a longitudinal axis of the distraction screw interface;

in a second state, the distraction screw fixates to the first member in a manner that forcibly captures the first member between the distraction screw along a superior surface of the first member and the first vertebra along the inferior surface of the first member.

12. A device as in claim 11, further comprising a bone screw interface configured to receive a bone screw for anchoring the device to the first and second vertebra, wherein the position of the distraction screw relative to the head of the bone screw is variable.

13. A bone fixation device for retaining bone structure in a desired spatial relationship, comprising:

a first member connectable to a first bone structure;

a second member connectable to a second bone structure and interconnected with the first member, wherein the first and second members are movable relative to one another across a range of motion;

a locking member that transitions between a first state wherein the locking member engages the first member, and a second state wherein the locking member engages the second member, wherein the locking member and the first member move in unison across a first distance when the locking member is in the first state, and wherein the locking member and the second member move in unison across a second distance when the locking member is in the second state; and an actuation member that is actuated to transition the locking member between the first state and the second state wherein the actuation member comprises a screw, wherein the locking member is in the first state when the screw is open and in the second state when the screw is closed.

14. A device as in claim 13, wherein at least a portion of the locking member protrudes through a hole in the first member when the locking member is in the first state.

15. A device as in claim 13, wherein at least a portion of the locking member abuts the second member when the locking member is in the first state.

16. A device as in claim 13, wherein the first distance is smaller than the second distance.

17. A device as in claim 13, further comprising at least one elongate rod interconnecting the first member and the second member.

18. A device as in claim 13, wherein the range of motion is linear.

19. A device as in claim 13, wherein the first member includes a distraction screw coupler that permits the first member or the first vertebra to be coupled to a distraction screw while the first member is connected to the first vertebra.

20. A device as in claim 13, wherein the first member includes a modular coupler that can mate with a second bone fixation device.

21. A bone fixation device for retaining bone structure in a desired spatial relationship, comprising:

a first member connectable to a first bone structure;

a second member connectable to a second bone structure and interconnected with the first member, wherein the first and second members are movable relative to one another across a range of motion;

a locking member that transitions between a first state wherein the locking member engages the first member, and a second state wherein the locking member engages the second member, wherein the locking member and the first member move in unison across a first distance when the locking member is in the first state, and wherein the locking member and the second member move in unison across a second distance when the locking member is in the second state; and an actuation member that is actuated to transition the locking member between the first state and the second state wherein the actuation member comprises a screw, wherein the locking member is in the first state when the screw is open and in the second state when the screw is closed;

wherein the first member includes a modular coupler that can mate with a second bone fixation device.

22. A device as in claim 21, wherein at least a portion of the locking member protrudes through a hole in the first member when the locking member is in the first state.

23. A device as in claim 21, wherein at least a portion of the locking member abuts the second member when the locking member is in the first state.

24. A device as in claim 21, wherein the first distance is smaller the second distance.

25. A device as in claim 21, further comprising at least one elongate rod interconnecting the first member and the second member.

26. A device as in claim 21, wherein the range of motion is linear.

27. A device as in claim 21, wherein the first member includes a distraction screw coupler that permits the first member or the first vertebra to be coupled to a distraction screw while the first member is connected to the first vertebra.

* * * * *

UNITED STATES PATENT AND TRADEMARK OFFICE
CERTIFICATE OF CORRECTION

PATENT NO. : 7,635,366 B2
APPLICATION NO. : 11/025659
DATED : December 22, 2009
INVENTOR(S) : M. Samy Abdou It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 368 days.

Signed and Sealed this

Ninth Day of November, 2010

David J. Kappos
*Director of the United States Patent and Trademark Office*